(12) United States Patent
Terwillegar et al.

(10) Patent No.: US 11,098,158 B2
(45) Date of Patent: Aug. 24, 2021

(54) HYBRID POLYOLS BASED ON NATURAL OIL POLYOLS

(71) Applicant: PTT Global Chemical Public Company Limited, Bangkok (TH)

(72) Inventors: Arne Matthew Terwillegar, Kernersville, NC (US); Thidarat Tosukhowong, Billerica, MA (US); Charliss Denniston, Belmont, MA (US); Nuttara Jamonnak, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 4 days.

(21) Appl. No.: 16/313,216

(22) PCT Filed: Jun. 27, 2017

(86) PCT No.: PCT/US2017/039562
§ 371 (c)(1),
(2) Date: Dec. 26, 2018

(87) PCT Pub. No.: WO2018/005538
PCT Pub. Date: Jan. 4, 2018

(65) Prior Publication Data
US 2020/0148817 A1    May 14, 2020

Related U.S. Application Data

(60) Provisional application No. 62/355,779, filed on Jun. 28, 2016, provisional application No. 62/404,085, filed on Oct. 4, 2016.

(51) Int. Cl.

| | |
|---|---|
| *C08G 18/18* | (2006.01) |
| *C08G 63/91* | (2006.01) |
| *C07C 69/675* | (2006.01) |
| *C08G 18/16* | (2006.01) |
| *C08G 18/24* | (2006.01) |
| *C08G 18/42* | (2006.01) |
| *C08G 18/76* | (2006.01) |
| *C08J 9/12* | (2006.01) |

(52) U.S. Cl.
CPC .......... *C08G 63/916* (2013.01); *C07C 69/675* (2013.01); *C08G 18/165* (2013.01); *C08G 18/1825* (2013.01); *C08G 18/244* (2013.01); *C08G 18/425* (2013.01); *C08G 18/4288* (2013.01); *C08G 18/7621* (2013.01); *C08J 9/125* (2013.01); *C08G 2110/005* (2021.01); *C08G 2110/0008* (2021.01); *C08G 2110/0083* (2021.01); *C08G 2350/00* (2013.01); *C08J 2205/06* (2013.01); *C08J 2375/06* (2013.01)

(58) Field of Classification Search
CPC ................ C07C 69/675; C08G 18/165; C08G 18/1825; C08G 18/244; C08G 18/4018; C08G 18/425; C08G 18/4288; C08G 18/7621; C08G 63/12; C08G 63/916; C08G 2110/0008; C08G 2110/005; C08G 2110/0083; C08G 2350/00; C08J 9/125; C08J 2205/06; C08J 2375/06; C08L 67/08
See application file for complete search history.

(56) References Cited

U.S. PATENT DOCUMENTS

| | | | | |
|---|---|---|---|---|
| 3,718,714 A | * | 2/1973 | Comstock et al. | ........... 525/170 |
| 2006/0276609 A1 | * | 12/2006 | Lysenko | ............ C08G 18/4841 528/44 |
| 2012/0277338 A1 | * | 11/2012 | Kaplan | .............. C08G 18/4072 521/157 |
| 2014/0275310 A1 | * | 9/2014 | Adkins | ................ C08G 18/636 521/164 |
| 2016/0102166 A1 | * | 4/2016 | Ni | ...................... C08G 18/4288 521/172 |

* cited by examiner

*Primary Examiner* — John M Cooney
(74) *Attorney, Agent, or Firm* — Oblon, McClelland, Maier & Neustadt, L.L.P.

(57) ABSTRACT

This invention relates to hybrid polyols useful in the manufacture of polyurethane. The hybrid polyols of the present invention is derived by copolymerizing or grafting a traditional polyester polyol onto a natural oil polyol. In the preferred embodiment of the present invention, the traditional polyester polyol grafted onto natural oil polyol contains a high level of bio-renewable content. The hybrid polyols of the present invention with high level of bio-renewable content is useful in the manufacture of polyurethane either alone or in combination with polyester polyol or polyether polyol derived from petrochemical sources.

18 Claims, 8 Drawing Sheets

HYBRID POLYOLS BASED ON NATURAL OIL POLYOLS

CROSS-REFERENCE TO RELATED APPLICATION

The application is the U.S. national stage application of International Patent Application No. PCT/US2017/039562, which claims the priority of the U.S. Provisional Application Ser. No. 62/355,779 filed on Jun. 28, 2016 and U.S. Provisional Application Ser. No. 62/404,085 filed on Oct. 4, 2016.

FIELD OF THE INVENTION

The present invention is in the field of flexible polyurethane foam manufacturing. More specifically, the present invention is related to the chemical synthesis of hybrid polyols with high level of biorenewable content useful in flexible polyurethane foam manufacturing.

BACKGROUND OF THE INVENTION

Flexible polyurethane foam is used extensively in a variety of applications requiring the unique mechanical, sound absorbing, load-bearing and/or other physical properties. Flexible polyurethane foams are made by the reaction of at least one polyisocyanate containing isocyanate (NCO) groups with at least one polyol containing hydroxyl (OH) groups in the presence of blowing agent(s), surfactant(s), catalyst(s) and other optional additives. The blowing agent most commonly used is water, which reacts with polyisocyanate to form carbon dioxide and polyurea. The polyurea is present along with the polyurethane resulting from the polyisocyanate-polyol reaction.

Flexible polyurethane foams are typically produced using either a slabstock foam manufacturing process or a molded flexible foam manufacturing process. Slabstock flexible foam is typically produced in either a high pressure or low pressure machine having a continuous mixer. Such continuous mixing machines may generally produce 100 pounds or more per minute of slabstock foam. In general, the production of slabstock foam involves the metering of a polyol-containing composition and a polyisocyanate-containing composition from separate feed lines (i.e., streams) via a mixing head having a pin mixer or high shear mixer into a trough. The product begins to froth and rise out of the trough and overflows onto fall plates. On the fall plates, the product continues to rise and contacts a conveyor. The product cures as the conveyor carries it along a length forming the slabstock foam. The conveyors are typically lined with a paper or plastic liner to allow for easy removal of the slabstock foam. As the foam exits the machine, it is cut into large blocks.

In general, molded flexible foam is typically produced by mixing a polyol-containing composition and a polyisocyanate-containing composition in a metered foam mixing and dispensing unit to form a foam intermediate composition and dispensing the foam intermediate composition into a sufficiently heated mold of desired design. The mold is typically vented to allow for the buildup and subsequent release of internal pressure. The mold has two or more sections with provisions for automatic opening and closing, and may be formed from cast aluminum or any other suitable material. Following the mixing and dispensing steps, the lid of the mold is closed and locked, and the foam intermediate composition is allowed to cure at a sufficient temperature, for a sufficient period of time. A sufficiently heated oven capable of receiving the mold may also be employed during the curing step. Once the curing step has completed, the lid of the mold is opened and the resultant foam product is removed and then transferred to a foam cell-crushing device which is used to apply pressure to the foam product in order to open the cells prior to being processed via other related finished-foam handling systems such as trimming and fabrication. During trimming and fabrication, the foam is converted into a finished product such as an automobile seating cushion.

Typically, slabstock and molded flexible foams are made from a polyether or polyester polyol, a polyisocyanate such as toluene diisocyanate, an amine catalyst, a tin catalyst, a blowing agent and other ancillary additives. Polyether polyols traditionally used to make polyurethane foam are generally derived from petroleum based raw materials. A standard polyether polyol used in the flexible slabstock foam industry is produced by reaction of ethylene or propylene oxide with glycerol in the presence of alkoxylation catalyst. Functionality, molecular weight and the alkoxide composition of the polyol (or polyol blend) can be adjusted to affect physical and/or processing properties of the foam produced.

Polyester polyols share a modicum of the flexible slabstock or molded polyurethane foam industry; their market share is a fraction due to increased cost and viscosities of the ester based materials. Their performance, however, is typically far superior to that of a polyether analog. Polyester based foams are preeminent in applications requiring superior solvent resistance, tensile strength, and often for flame lamination.

The flexible foam industry has witnessed a significant increase in the use of biobased polyols, which are incorporated into a formulation in the place of a petroleum based polyether or polyester polyol. The polyurethane foam products with certain level of biobased polyols have competitive marketing advantage relative to those products prepared solely with the raw materials derived from petroleum. Additionally, the biobased polyols have cost stability due to readily available feedstock. As a result, the flexible polyurethane foam manufacturers prefer to use higher proportion of biobased polyols in the flexible polyurethane foam products.

Biobased polyols are typically derived from natural oil present in the plant seeds. In terms of their chemical identity, the natural oils are triglycerides with fatty acid side chains each with 10-22 carbons. In general, the fatty acid side chains in triglycerides with the exception of castor oil have no functional groups and are not reactive to polyisocyanates. The hydroxyl groups in the castor oil are responsible for the reaction of castor oil with polyisocyanate and are referred to as "hydroxyl functionality" or "functionality" of natural oils. The natural oils which lack functionality are subjected to one or other chemical transformation procedures to introduce functionality and the resulting product is referred as functionalized natural oil or natural oil polyol. The list of chemical reactions that can be used to introduce functionality in natural oil includes transesterification with functionalized materials, epoxidation and ring opening, oxidation, ozonolysis and hydroformylation. The added reactive functionality could be any active hydrogen moiety, and is typically a hydroxyl group or an amine. A number of chemical modifications to introduce functionality to triglycerides have been reported in a number of patent documents and all of which are incorporated herein by reference. U.S. Pat. Nos. 6,107,433 and 6,121,398 describe the epoxidation procedure to introduce functionality in natural oil. The International Patent Application Publication No. WO 2003/029182 describes the hydroxylation procedure to introduce functionality in triglycerides. U.S. Pat. Nos. 6,897,283, 6,962,636 and 6,979,477 describe the esterification procedure to introduce functionality in triglycerides. The International Patent Application Publication No. WO 2004/096744 describes the hydroformylation procedure to introduce functionality in triglycerides. U.S. Pat. No. 4,640,801 describes the grafting procedure to introduce functionality in triglycerides. U.S. Pat. No. 6,433,121 describes the consecutive two-step process involving epoxidation and hydroxylation procedure to introduce functionality in the triglycerides. U.S. Pat. No. 4,534,907 and the International Patent Application No. WO 2004/020497 describe the alkoxylation procedure to introduce functionality in triglycerides. The above cited references for modifying the natural oil are incorporated herein by reference.

There are challenges for the use of functionalized natural oils (also known as "natural oil Polyol" or "NOP") as a polyol component in the manufacture of flexible polyurethane foam products. The mechanical strength properties such as tear strength, tensile strength and elongation ("TTE"), Ball Rebound, Compression Force Deflection (CFD) and Compression Set of foams formed from the reaction of functionalized natural oils with isocyanate are typically inferior relative to foams made solely from petrochemical polyols. The problems with the use of typical natural oil polyols in the polyurethane foam manufacture are two-fold: (1) The alcohol groups in the polyols derived from petroleum are primary which are 3.3 times more reactive with isocyanates than the secondary alcohols in the NOPs; and (2) The saturated fatty acid in the natural oil polyols is not reactive and adversely impacts the properties of polyurethane foams. These physical properties effectively limit the amount of natural oil polyol that can be incorporated into a flexible foam formulation.

U.S. Patent Application Publication No. 2012/0277338 describes a method of trans-esterifying a polyester polyol, preferably aromatic polyester polyol, with a natural oil polyol or natural oil such as soybean oil to improve the physical properties.

U.S. Pat. No. 9,260,346 describes a technique of grafting an acrylic polyol onto a natural oil polyol in order to increase the physical properties. U.S. Pat. No. 8,828,269 describes a technique of esterifying mono-glycerides into a natural oil polyol to increase its performance. U.S. Pat. No. 8,765,828 describes a method of blending in a thermoplastic acrylic powder into the foaming matrix to increase resilience. U.S. Pat. No. 8,541,536 describes a coupling of natural oil polyols via esterification monomers. These approaches do address the deficiencies associated with the use of natural oil polyols in the manufacture of polyurethane foams. However, these modified natural oil polyols, due to the relative low ester content, neither exhibit desirable mechanical properties nor the compatibility with the polyols derived from petroleum sources. In view of the foregoing, a method that improves the mechanical strength of flexible foams made from biobased polyol and allows the use of higher concentrations of biobased polyols without resulting in a loss of mechanical strength would represent a significant advancement in the art of flexible polyurethane foam manufacturing. The present invention provides a procedure to build an ester onto a natural oil polyol as opposed to trans-esterifying a natural oil polyol. The procedure described in the present invention yields a co-polyester polyol, also referred as a hybrid polyol based on natural oil polyol, with improved performance. In addition, the hybrid polyols based on natural oil polyols prepared according to the present invention contain high proportion of biorenewable content. Furthermore, the option of blending these hybrid polyols based on natural oil polyols with the conventional polyether polyols derived from petrochemical sources using an incumbent technology without fear of phase separation is an improvement in the art.

SUMMARY OF THE INVENTION

This present invention provides a process for manufacturing flexible polyurethane foam with a high level of biorenewable content. More specifically, the present invention provides a co-polyester polyol, also referred as a hybrid polyol based on natural oil polyol, with the high biorenewable content useful in the preparation of the flexible polyurethane foam. Triglycerides derived from plant sources such as natural oil, fatty acids from animal sources and polycarboxylic acids and polyhydric alcohols derived from fermentation process using biological feedstocks such as carbohydrates and cellulosic hydrolysate are used in the preparation of co-polyester polyols of the present invention with high percentage of biorenewable content. The co-polyester polyols with high percentage of biorenewable content can be reacted with isocyanate to manufacture flexible polyurethane foam. The co-polyester polyols with high percentage of biorenewable content manufactured as per the present invention are suitable for use on their own or can be used as a mixture with polyester polyols and polyether polyols derived from petroleum feedstock in the manufacture of flexible polyurethane foam.

In one embodiment of the present invention, the triglycerides derived from plant seeds as natural oil are subjected to chemical reactions so that certain functional groups such as carboxyl and hydroxyl groups are inserted into the fatty acid side chains in place of ethylenically unsaturated double bonds leading to the formation of natural oil polyols also referred as functionalized natural oil. The functionalized natural oil is reacted with one or more polycarboxylic acid and one or more polyhydric alcohol in the presence of an esterification catalyst to yield a co-polyester polyol, also referred as hybrid polyols, with functionality and hydroxyl number in a specific range. Moreover, by means of selecting appropriate source of polycarboxylic acid and polyhydric alcohol, it is also possible to control the range of biorenewable content in the resulting co-polyester polyol.

In one aspect of this embodiment, the co-polyester polyol of the present invention is reacted with polyisocyanate to yield flexible polyurethane foam. In another aspect of this invention, the co-polyester polyol prepared according to the present embodiment is mixed with polyol derived from petrochemical source. The combined mixture of co-polyester polyol of the present invention and polyol derived from petrochemical source is reacted with polyisocyanate to yield flexible polyurethane foam with the biorenewable content proportional to the biorenewable content in the co-polyester polyol in the mixture. In preparing a mixture with the co-polyester polyol of this embodiment, either a polyester polyol derived from petrochemical sources or a polyether polyol derived from petrochemical source is used. In a preferred aspect of the present embodiment, the polyol mixture used in the preparation of flexible polyurethane foam contains the polyester polyol derived from petrochemical source and the co-polyester polyol prepared according to the present embodiment.

In another embodiment of the present invention, a co-polyester polyol is prepared by following a method involving free radical mediated grafting of an ethylenically unsaturated monomer to an ethylenically unsaturated fatty acid side chain in a triglyceride molecule. In one aspect of this embodiment, an ethylenically unsaturated dicarboxylic acid is used as a monomer in the free radical mediated grafting reaction to yield functionalized natural oil also referred as natural oil polyol. In another aspect of the present embodiment, an ethylenically unsaturated diol is used as a monomer in the free radical mediated grafting reaction to yield functionalized natural oil also referred as natural oil polyol. As result of the free radical mediated grafting reaction, the ethylenically unsaturated monomer is grafted onto a double bond in the fatty acid side chain to introduce two functional groups in the place where there was a double bond. When an ethylenically unsaturated dicarboxylic acid is used in the grafting reaction, two carboxyl functional groups are added. On the other hand, when an ethylenically unsaturated diol is used in the grafting reaction two hydroxyl functional groups are added. The newly added functional groups help in the initiation of the esterification reaction when provided with one or more polycarboxylic acids, one or more polyhydric alcohols and an esterification catalyst. By means of controlling the ratio of functionalized natural oil produced according to this embodiment, polycarboxylic acid and polyhydric alcohol, a co-polyester polyol is produced with functionality and hydroxyl number in a specific range. Moreover, by means of selecting appropriate sources of polycarboxylic acid and polyhydric alcohol, it is also possible to control the amount of bio-renewable content in the resulting co-polyester polyol.

In one aspect of this embodiment, the co-polyester polyol produced using free radical mediated grafting reaction is reacted with polyisocyanate to yield flexible polyurethane foam. In another aspect of this invention, the co-polyester polyol prepared according to the present embodiment is mixed with polyol derived from petrochemical source to yield a polyol mixture. The combined mixture of co-polyester polyol and polyol derived from petrochemical source is reacted with polyisocyanate to yield flexible polyurethane foam with the biorenewable content proportional to the biorenewable content in the co-polyester polyol in the mixture. In preparing the polyol mixture of this embodiment, either a polyester polyol derived from petrochemical sources or a polyether polyol derived from petrochemical source is used. In a preferred aspect of the present embodiment, the polyol mixture used for the preparation of polyurethane foam contains the polyester polyol derived from petrochemical source and the co-polyester polyol prepared using free radical mediated grafting reaction.

In another embodiment of the present invention, either of the two types of the co-polyester polyols prepared according to the present invention is mixed with isosorbide based polyester polyol and used in the preparation of flexible polyurethane foam. The isosorbide-based polyester polyol is prepared through an esterification reaction involving biobased isosorbide, biobased succinic acid and biobased 1, 3-propanediol, all derived from renewable biological materials through biological fermentation process.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations and equivalents in form and function, as will occur to those skilled in the art and having the benefit of this disclosure.

DETAILED DESCRIPTION OF THE PREFERRED EMBODIMENTS

Figure 1:
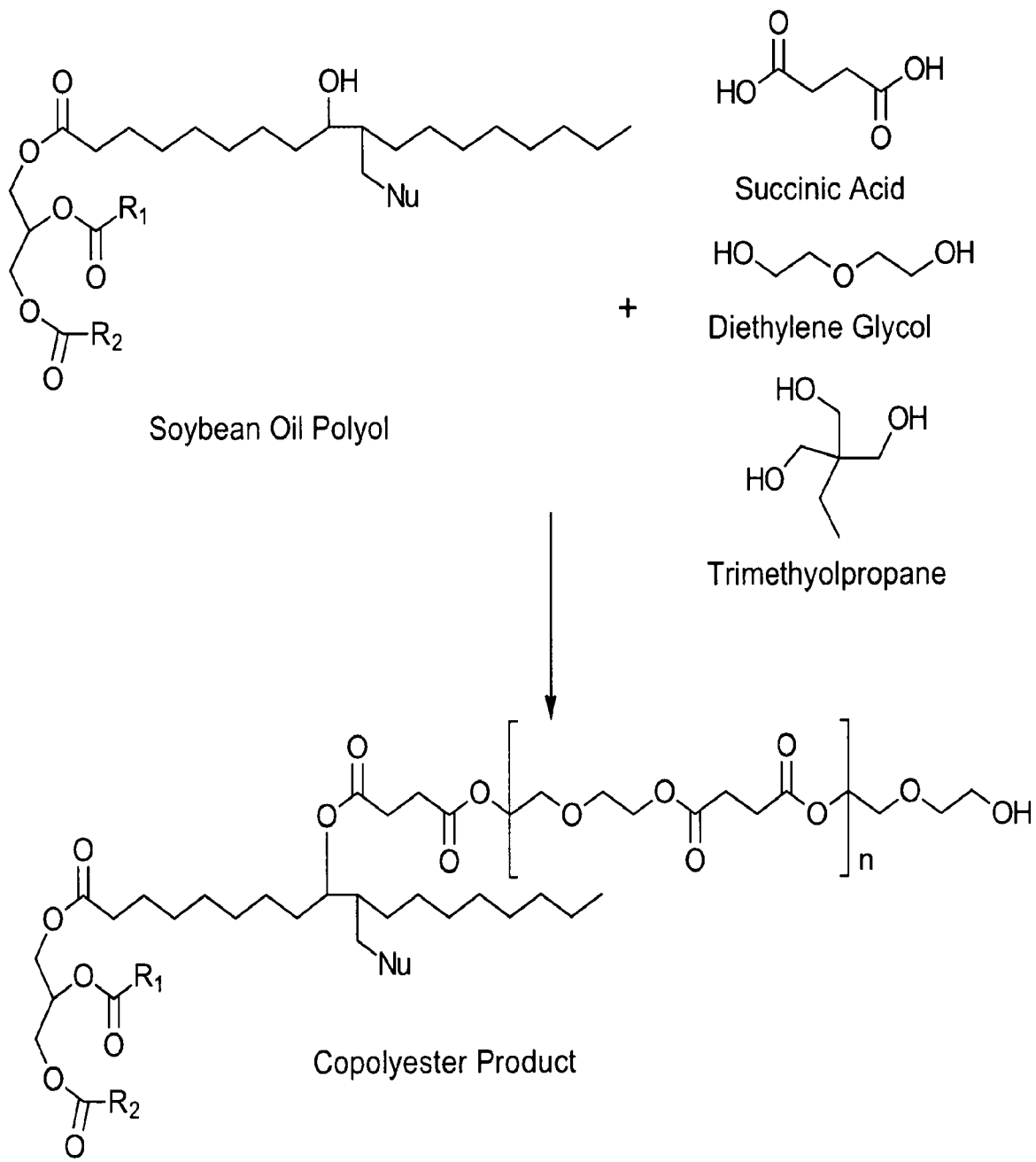
FIG. 1. Preparation of a hybrid polyol. Commercially available natural oil polyol (Agrol®—Soybean oil polyol produced by BioBased Technologies) is reacted with succinic acid, diethylene glycol and optionally trimethylolpropane or glycerol in the presence of an esterification catalyst to yield a hybrid polyol. The incorporation of trimethylolpropane or glycerol is expected to cause branching in the resulting hybrid polyol although it is not illustrated in the figure. Both the natural oil polyol and succinic acid used in this reaction are derived from biorenewable sources. The biorenewable content of the resulting hybrid polyol is proportional to the content of natural oil polyol and succinic acid.
Figure 2:
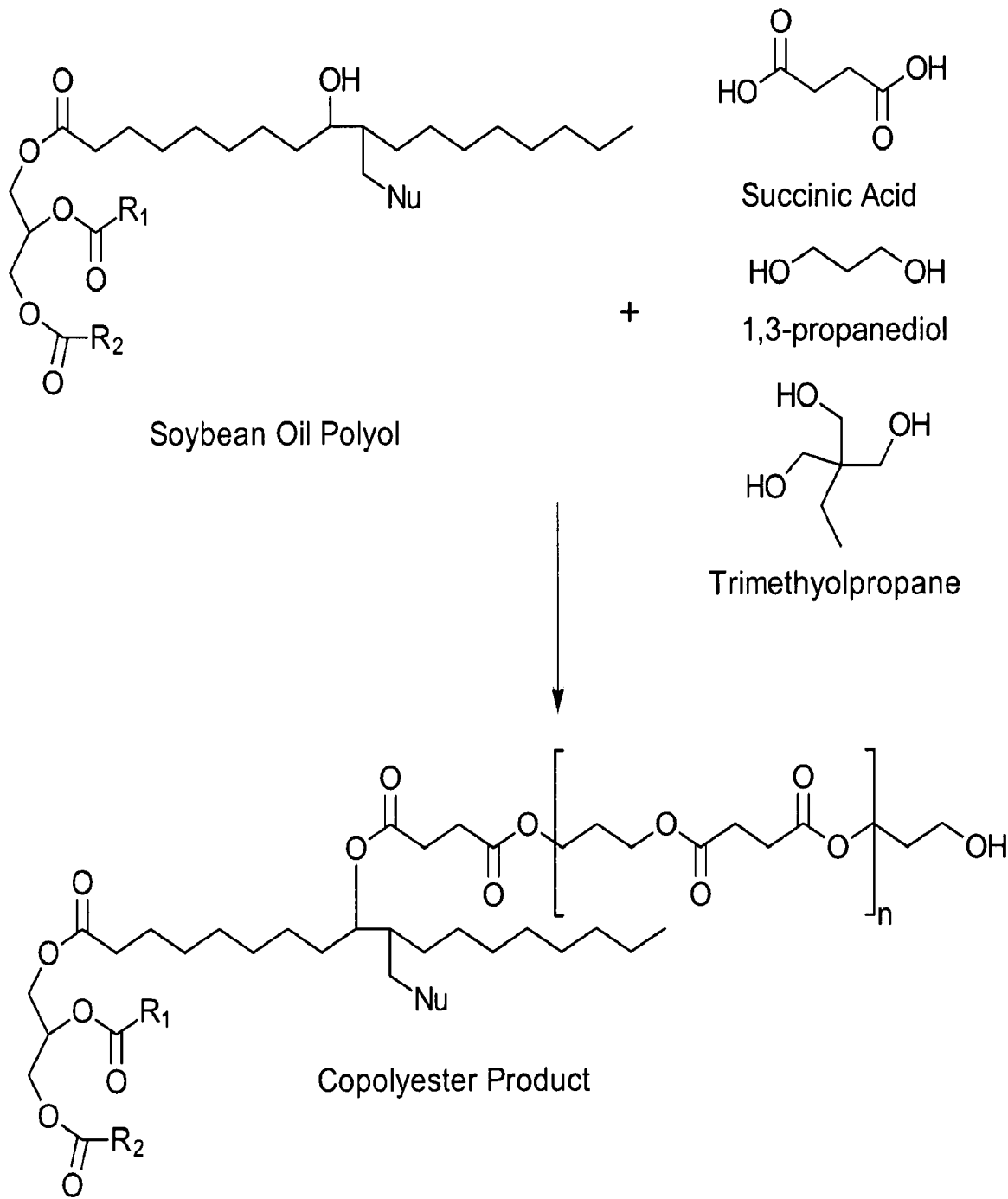
FIG. 2. Preparation of a hybrid polyol. Commercially available functionalized natural oil polyol (Agrol®—Soybean oil polyol produced by BioBased Technologies) is reacted with succinic acid, 1, 3-propanediol and optionally trimethylolpropane or glycerol in the presence of an esterification catalyst to yield a hybrid polyol. The incorporation of trimethylolpropane or glycerol is expected to cause branching in the resulting hybrid polyol although it is not illustrated in the figure. The natural oil polyol, 1, 3-propanediol and succinic acid used in the reaction are derived from biorenewable sources. The biorenewable content of the resulting hybrid polyol is proportional to the content of natural oil polyol, 1, 3-propanediol and succinic acid.
Figure 3:
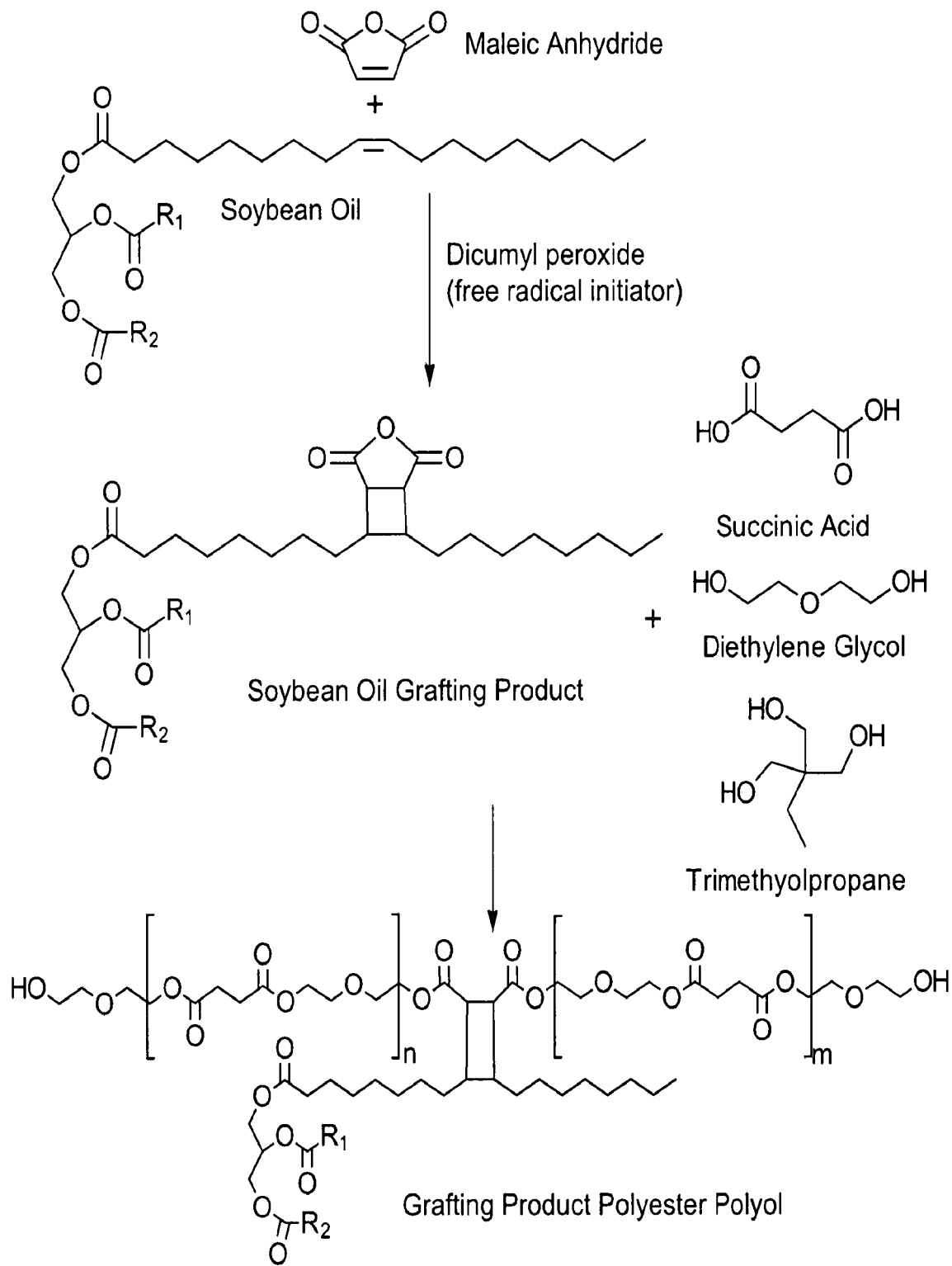
FIG. 3. Preparation of a hybrid polyol by means of free radical mediated grafting reaction. In this reaction, virgin soybean oil with an ethylenically unsaturated double bond is reacted with maleic anhydride having an ethylenically unsaturated double bond in the presence of a free radical initiator (dicumyl peroxide) to yield a product wherein the maleic anhydride is grafted onto soybean oil. The resulting product has two functional carboxyl groups which can participate in further esterification reaction when provided with succinic acid, diethylene glycol, trimethylolpropane or glycerol and an esterification catalyst. At the end of the esterification reaction, a hybrid polyol with free hydroxyl functional groups is produced. The incorporation of trimethylolpropane or glycerol into this hybrid polyol is expected to cause branching in the resulting hybrid polyol although it is not illustrated in the figure. The natural oil and succinic acid used in this reaction are derived from biorenewable sources. The bio-renewable content of the resulting hybrid polyol is proportional to the content of natural oil and succinic acid.
Figure 4:
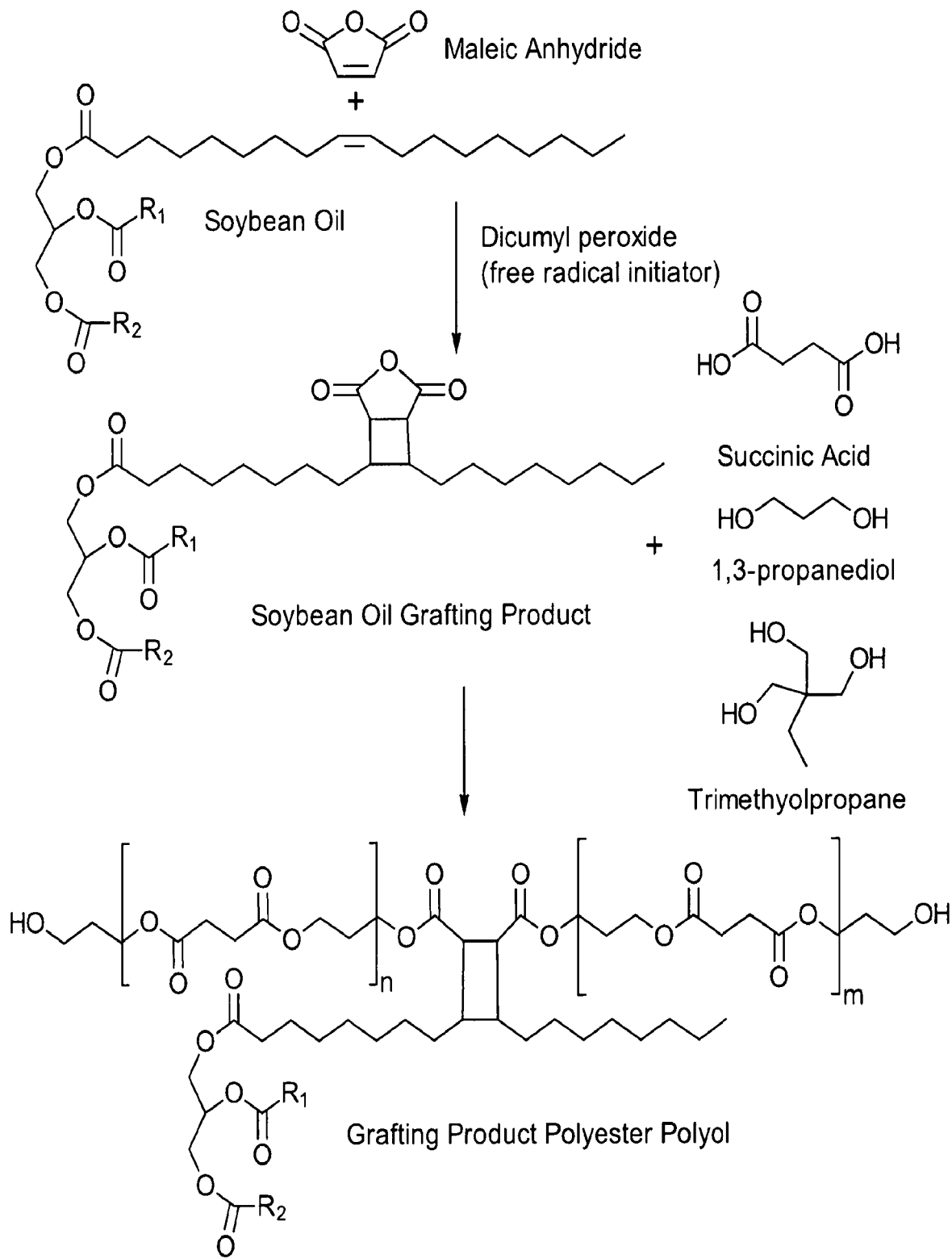
FIG. 4. Preparation of a hybrid polyol by means of free radical mediated grafting reaction. In this reaction, virgin soybean oil with an ethylenically unsaturated double bond is reacted with maleic anhydride having an ethylenically unsaturated double bond in the presence of a free radical initiator (dicumyl peroxide) to yield a product wherein the maleic anhydride is grafted onto soybean oil. The resulting product has two functional carboxyl groups which can participate in further esterification reaction when provided with succinic acid, 1, 3-propanediol, trimethylolpropane or glycerol and an esterification catalyst. At the end of the esterification reaction, a hybrid polyol with free hydroxyl functional groups is produced. The incorporation of trimethylolpropane or glycerol is expected to cause branching in the resulting hybrid polyol although it is not illustrated in the figure. The natural oil, 1, 3-propanediol and succinic acid used in this reaction are derived from biorenewable sources. The biorenewable content of the resulting hybrid polyol is proportional to the content of natural oil, 1, 3-propanediol and succinic acid.
Figure 5:
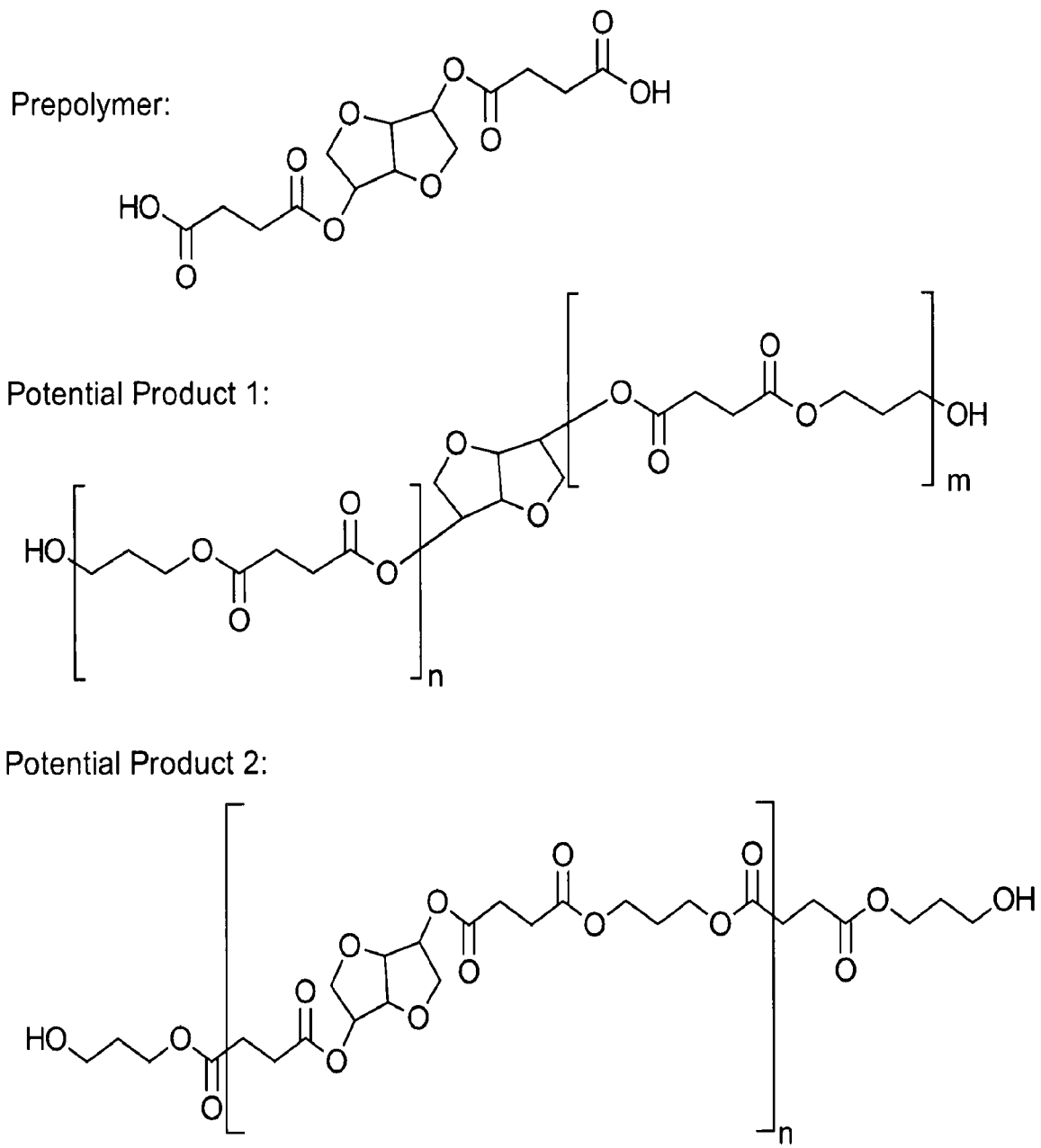
FIG. 5. Preparation of isosorbide-based polyester. Biobased isosorbide and biobased succinic acid, derived through biological fermentation processes, are mixed together in the presence of an esterification catalyst to yield isosorbide ester monomer (prepolymer) comprising both starting components (A). In the next stage, 1,3-propanediol is added and, through a polymerization reaction many different types of isosorbide-based polyesters are produced. In one aspect of the present invention, starting with the isosorbide ester monomer polyester chain extension happens at both the ends involving the use of only biobased succinic acid and biobased 1, 3-propanediol (B). In another aspect of the present invention, the polymerization reaction involves the use of isosorbide ester monomer (A) and results in a polyester polyol having all three components, namely biobased isosorbide, biobased succinic acid and biobased 1, 3-propanediol in equal proportion (C). The polymers illustrated in this figure are merely representative structures and should not be considered as wholly inclusive of all isosorbide-based polyester preparations that can be made. It is possible for those skilled in the art to perform esterification reactions in such a way to obtain polyol molecules comprising these three basic components (biobased isosorbide, biobased succinic acid, and biobased 1,3-propanediol) in varying proportion and in varying configurations.

A biobased hybrid polyol of the present invention comprises at least one functionalized natural oil (also referred to as natural oil polyol) or functionalized natural oil-derived fatty acid and/or fatty acid ester containing isocyanate-reactive primary or secondary hydroxyl groups and a functionality of at least about 1.5, preferably at least about 2.0.

The term "biobased" as used in this invention refers to origin of a particular chemical entity which may either be a single molecule such as succinic acid or a compound such as a polyester polyol. When chemical molecule or a compound is derived from biological materials, it is referred as biobased chemical molecule or a compound as the case may be. Thus when succinic acid and 1, 3-propanediol molecules are produced through biological fermentation process using renewable biological materials, they are referred as biobased succinic acid and biobased 1, 3-propanediol. When biobased succinic acid and biobased 1, 3-propanediol are reacted in the presence of an esterification catalyst, the resulting polyester molecule, polypropylene succinate is also referred as biobased polypropylene succinate. In the same way, the biobased succinic acid, biobased 1, 3-propanediol and a natural oil polyol are reacted to produce a biobased hybrid polyol. The term "biorenewable" is also used interchangeably with the term "biobased".

The biobased chemicals are derived from renewable biological materials. As defined in this invention, the term "renewable biological materials" include any feedstock derived from plant or animal materials as opposed to the materials derived from petrochemical feedstock. The term "renewable biological material" is also used interchangeably with the term "biomass". The term "biomass" as used in the present invention refers to carbohydrates, sugars, glycerol and lignocellulosic materials derived from renewable plant resources which can be used in the fermentative production of monomers such as succinic acid and 1, 3-propanediol useful in the present invention. The monomers such as succinic acid, 1, 3-propanediol and its derivatives obtained from renewable biological materials through a biological fermentation process are referred to as "biomass-derived" or "biobased chemicals". On the other hand, succinic acid, 1, 3-propanediol and its derivatives obtained from petrochemical feedstock through chemical means are referred as "petrochemical derived" or "petrochemical based".

The biobased monomers useful in the present invention can be distinguished from monomers manufactured following the traditional chemical methods involving petroleum feedstock on the basis of their carbon 14 content following the method ASTM-D6866 provided by American Society of Testing and Materials. Cosmic radiation produces $^{14}C$ ("radiocarbon") in the stratosphere by neutron bombardment of nitrogen. $^{14}C$ atoms combine with oxygen atom in the atmosphere to form heavy $^{14}CO_2$, which, except in the radioactive decay, is indistinguishable from the ordinary carbon dioxide. $CO_2$ concentration and the $^{14}C/^{12}C$ ratio is homogeneous over the globe and because it is used by the plants, the ratio $^{14}C/^{12}C$ is retained by the biomass while the content of $^{14}C$ in the fossil materials, originally derived from photosynthetic energy conversion, has decayed due to its short half-life of 5730 years. By means of analyzing the ratio of $^{14}C$ to $^{12}C$, it is possible to determine the ratio of fossil fuel derived carbon to biomass-derived carbon. International Patent Application Publication No. WO2009/155085 A2 and U.S. Pat. No. 6,428,767 provide details about the use of ASTM-D6866 method for determining percent of biomass-derived carbon content in a chemical composition. The details related to carbon dating disclosed in the U.S. Pat. No. 6,428,767 is incorporated herein by reference. An application note from Perkin Elmer entitled "Differentiation between Fossil and Biofuels by Liquid Scintillation Beta Spectrometry—Direct Method" provides details about the methods involving ASTM Standard D6866.

The term "natural oil" as used herein includes, but is not limited to, vegetable oils, algae oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, carnellina oil, and castor oil. Representative non-limiting examples of animal fats include lard, tallow, poultry fat, yellow grease, and fish oil. Tall oil, a by-product of wood pulp manufacturing process, is also useful in the present invention. In certain embodiments, the natural oil may be partially hydrogenated. In other embodiments, the natural oil may be refined, bleached, and/or deodorized.

The term "functionalized" is used herein in its broadest sense and is intended to cover natural oils as well as the fatty acids and/or fatty acid esters derived from those natural oils that contain connate hydroxyl groups. Certain natural oils and the fatty acids derived from thereof (such as castor oil and the ricinoleic acid derived from thereof) contain connate hydroxyl groups when they are produced in the plants. When a natural oil and the fatty acids and/or fatty acid esters derived from said natural oil do not contain connate hydroxyl groups, they are chemically modified to impart hydroxyl functionality thereto. When natural oil that does not contain connate hydroxyl groups is chemically modified to have hydroxyl groups, it is referred as natural oil polyol. The biobased natural oil polyol possesses a hydroxyl value (OH) ranging from about 25 to about 230, particularly from about 40 to about 130, more particularly from about 70 to about 80 mg KOH/g.

A number of chemical routes can be followed to functionalize natural oils. One of the routes that can be followed in the functionalization of natural oil involves the epoxidation of the double bond in the natural oil followed by the step of nucleophilic ring opening reaction. At the end of nucleophilic ring opening reaction, one or more hydroxyl functional group is added to the natural oil owing to the nucleophile addition. The most common method for epoxidation of the natural oil is based on peracetic acid formed in situ from reaction between acetic acid and hydrogen peroxide, with ion-exchange resin catalyst, at 60° C. in toluene for 12 h. Natural oil can also be epoxidized by micro-waves with 90% yield within 5 minutes. Epoxidation through enzymatic reaction is also possible. Epoxide ring opening can be performed using sulfuric acid and water at 65° C. In another method, the epoxide ring opening reaction is carried out using methanol in water, with fluoroboric acid catalyst by means of maintaining the sample between 50° C. and 65° C. for 30 minutes. In the instant invention, the epoxide ring opening is achieved by using one or other polyfunctional carboxylic acid or polyhydric alcohol which is also used as a building block in the preparation of the hybrid polyols based on natural oil.

The biobased hybrid polyol prepared according to the present invention possesses a viscosity ranging from about 2000 to about 6000 centipoise at 25° C. The biobased component will typically represent at least about 5 weight percent of the polyol components present in the polyol-containing composition. For example, the biobased components may represent about 5, about 10, about 15, about 20, about 25, about 30, about 35, about 40, about 50, about 60, about 70, about 80, about 90 and even 100 weight percent of the polyol components present in the polyol-containing composition.

The biobased polyol can be prepared by epoxidizing natural oil and subsequently reacting the epoxidized natural oil with water and/or a hydroxylated material to convert the epoxy groups to hydroxyl groups. Biobased polyols based on epoxidized natural oils are commercially available, or alternatively can be prepared by reacting unsaturated natural oils with a peroxyacid to form the epoxidized oil. Suitable materials for use in converting the epoxy groups to hydroxyl groups (ring opening agents) include any reactive hydrogen compounds such as hydrogen, water, lithium aluminum hydride, sodium borohydride, ammonia, or aliphatic or aromatic amines, aliphatic or aromatic alcohols and their alkoxides (mono functional), glycols, triols, tetraols, sugars, carboxylic acids and mineral acids, including, for example, hydrochloric, sulfuric, and phosphoric acids. In the preparation of functionalized natural oil, an amount of ring opening agent is reacted with the epoxidized triglyceride sufficient to convert from about 10% to about 100% of the epoxy groups to hydroxyl groups. The hydroxylation of the epoxidized natural oil can take place at temperatures ranging from about 50° C. to about 250° C. and at pressures ranging from 0 to about 4000 psi. The resulting natural oil polyol may have an hydroxyl value ranging from about 25 to about 500 mg KOH/g and an acid value of from 0 to about 10 mg KOH/g.

Functionalized natural oils (also referred as natural oil polyols) are available commercially. They may comprise one or more natural oils or the fatty acids and/or fatty acids derived from the natural oils that have been epoxidized and then reacted with one or more mono-ols and/or diols to form a biobased polyol having primary or secondary hydroxyl groups. The list of commercially available biobased polyols that may be employed within the practice of the present invention include biobased polyols sold by Cargill under the tradename BiOH®, the biobased polyol sold by BioBased Technologies under the trade name Agrol® and the biobased polyol sold by Urethane Soy Systems under the trade name of SOYOL®.

The list of functionalized natural oils (also referred as natural oil polyols) suitable for the present invention includes castor oil, functionalized castor oil, functionalized coconut oil, functionalized cochin oil, functionalized corn oil, functionalized cottonseed oil, functionalized linseed oil, functionalized olive oil, functionalized palm oil, functionalized palm kernel oil, functionalized peanut oil, functionalized soybean oil, functionalized sunflower oil, functionalized tall oils, functionalized tallow, functionalized *lesquerella* oil, functionalized tung oil, functionalized whale oil, functionalized tea seed oil, functionalized sesame seed oil, functionalized safflower oil, functionalized rapeseed oil, functionalized fish oils, derivatives thereof, and combinations thereof.

Non-functionalized natural oils are also available commercially. They may comprise one or more natural oils and/or fatty acids derived from the natural oils. The list of natural oils suitable for the present invention includes castor oil, coconut oil, cochin oil, corn oil, cottonseed oil, linseed oil, olive oil, palm oil, palm kernel oil, peanut oil, soybean oil, sunflower oil, tall oils, tallow, *lesquerella* oil, tung oil, whale oil, tea seed oil, sesame seed oil, safflower oil, rapeseed oil, fish oils, derivatives thereof, and combinations thereof.

In one embodiment of the present invention, a soybean derived natural oil polyol is reacted with biobased succinic acid, biobased 1, 3-propanediol and (optionally) glycerol. The reactants are charged and reacted in a fashion as to reduce or eliminate the secondary hydroxyls present in the natural oil polyol and replace them with primary hydroxyls on the 1,3-propanediol. While slight transesterification prevents 100% conversion of the secondary hydroxyls, the amount is decreased relative to the amount originally present in the natural oil polyol. In accordance with this embodiment, the natural oil polyol Agrol® 3.0 (produced by BioBased Technologies, with a calculated functionality of 3.0 and a reported hydroxyl number of 115 mg KOH/g) is reacted with biobased succinic acid, biobased 1,3-propanediol and an esterification catalyst. The reaction is carried out at 205° C. for 12 hours or until all water has been eliminated. Also in accordance with this embodiment, Agrol® 3.0 is also reacted with biobased succinic acid, diethylene glycol and an esterification catalyst. The reaction is carried out at 205° C. for 12 hours or until all water has been eliminated. Further, in accordance with this embodiment, a natural oil Agrol® 3.0. is reacted with ortho-phthalic anhydride, 1,3-propanediol, and an esterification catalyst. The reaction is carried out at 205° C. for 12 hours or until all water has been eliminated.

In another embodiment of the present invention, soybean oil, prior to any modification, is reacted with maleic anhydride in the presence of a free radical peroxide initiator and a solvent and a chain transfer agent (CTA). The reaction is carried out at 150° C. for three hours or until all double bonds in the starting material have been eliminated as determined via analysis through IR spectroscopy.

In another embodiment of the present invention, the product of reaction between maleic anhydride and soybean oil is further esterified with biobased succinic acid, diethylene glycol and an esterification catalyst. The reaction is carried out at 210° C. for 12 hours or until all water has been eliminated.

In another embodiment of the present invention, the product of reaction between maleic anhydride and soybean oil is further esterified with biobased succinic acid, biobased 1, 3-propanediol and an esterification catalyst. The reaction is carried out at 210° C. for 12 hours or until all water has been eliminated.

Alternately, the esterification reactions involving natural oil polyol can be conducted with a range of monomers for polyester synthesis. A number of polyfunctional carboxylic acid and polyhydric alcohols may be used. The list of polyfunctional carboxylic acids (or their alkyl esters) suitable for the present invention includes but not be limited to: succinic acid, glutaric acid, pimelic acid, undecanoic acid, dodecanoic acid, dodecanedioic acid, subaric acid, azelaic acid, sebacic acid, adipic acid, phthalic anhydride; dimethyl terephthalate, terephthalic acid, isophthalic acid, 1,8-naphthalic anhydride, 1,8-naphthalic dicarboxylic acid, 1,8-dimethyl naphthalate, dimethyl isophthalate, phthalic acid, dimethyl terephthalate bottoms, phthalic anhydride bottoms, pyromellitic anhydride, mellitic anhydride, mellitic acid, trimellitic anhydride, 3,3'4,4'-benzophenone tetracarboxylic anhydride, 3,3'4,4'-benzophenone tetracarboxylic acid, trimellitic acid, polyethylene terephthalate recycled polymer, polybutylene terephthalate recycled polymer, polyethylene terephthalate virgin polymer, polybutylene terephthalate virgin polymer, mixtures thereof and the like. In preferred embodiments of the present invention, biobased polyfunctional carboxylic acids are used.

Examples of polyhydric alcohols suitable for use in preparing aromatic or aliphatic polyester polyols according to the present invention include glycerol, ethylene glycol, diethylene glycol, triethylene glycol, tetraethylene glycol, propylene glycol, dipropylene glycol, tripropylene glycol, tetrapropylene glycol, trimethylene glycol, 1,1,1-trimethylol ethane, 1,2,3-trimethylolpropane, pentaerythritol, and poly (oxyalkylene) polyols in which each repeating unit contains two to four carbon atoms derived from the polyaddition of ethylene oxide, propylene oxide, or butylene oxide and mixtures thereof. In preferred embodiments of the present invention, biobased polyhydric alcohols are used.

The free radical initiator useful in the present invention is peroxide or may include a combination of peroxides. The peroxide may include the "group" The peroxide may alternatively include the general formula:

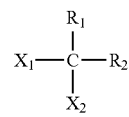

wherein each of $R_1$ and $R_2$ comprises one of an alkyl group, an oxygen-alkyl group and an oxygen-oxygen-alkyl group, $X_1$ comprises one of an ester group, an oxygen, and an alkyl group, and $X_2$ comprises a methyl group or a hydrogen so long as $X_1$ is an ester group. Typically, the peroxide includes monoperoxycarbonates, peroxyketals, and combinations thereof.

The free radical initiator can exhibit diimide functionality, i.e., the free radical initiator is an "azo" free radical initiator. In this example, the free radical initiator typically includes 2, 2'-azobis (2-methylbutanenitrile) that is commercially available from DuPont under the trade name of VAZO. The free radical initiator is typically provided in an amount of from 0.01 to 5 and alternatively from 0.1 to 1, parts by weight, each per 100 parts by weight of the polymerizable monomer.

A chain transfer agent is added to mitigate polymerization. The chain transfer agent is a typically a thiol. The chain transfer agent is selected from the group of alkanethiols, mercaptocarboxylic acids, hydroxylmercaptans, aminomercaptans, carboxyl sulfides, sulfide acid anhydrides, salts thereof, and combinations thereof. The chain transfer agent is typically provided in an amount of from 0.1 to 5 and alternatively from 0.1 to 2, parts by weight, each per 100 parts by weight of the polymerizable reactants.

The present invention also provides the process for producing flexible polyurethane foams from the hybrid polyols described herein using a polyisocyanate, a blowing agent, catalyst(s) and one or more optional additives or auxiliary compounds. The inventive hybrid polyols of the present invention has certain special advantages over the biobased natural oil polyols traditionally used to produce flexible polyurethane foams with certain percentage of renewable biobased component. In general, the polyurethane foams prepared using the traditional natural oil polyol often exhibit an odor, especially under exothermal slab-stock conditions while polyurethane foams produced using the hybrid polyol produced according to the present invention are found to be odor-free. Another advantage of the hybrid polyol of the present invention is its compatibility with petrochemical-derived polyether polyols generally used in the preparation of flexible polyurethane foams. Most of the traditional natural oil polyols when mixed with petrochemical derived polyether polyols show phase separation over time and require mixing before using the mixture for flexible polyurethane foam preparation. On the other hand, the hybrid polyols of the present invention mix freely with the petrochemical-derived polyether polyol and remain homogenous indefinitely. The hybrid polyol of the present invention is also found to be compatible with the isosorbide based polyester polyols. Moreover, the fact the hybrid polyol of the present invention comprises three different components linked through three different polyol chemistries allows us to tailor fit this co-polyester polyol to maximize strength of a particular chemistry that would benefit the application in question. For example, in the preparation of polyurethane foams to be exposed to aqueous environments, polyester portion may be minimized, while in applications requiring solvent resistance the polyester portion may be maximized.

The polyisocyanates which may be used in the present invention include aliphatic, cycloaliphatic, arylaliphatic and aromatic polyisocyanates having at least 2 isocyanate groups. For the production of flexible slabstock foam, aromatic polyisocyanates are preferred. Examples of suitable aromatic polyisocyanates include the 4,4'-, 2,4' and 2,2'-isomers of diphenylmethane diisocyanate (MDI), blends thereof, polymeric and monomeric MDI blends, toluene-2,4- and 2,6-diisocyanates (TDI), m- and p-phenylenediisocyanate, chlorophenylene-2,4-diisocyanate, diphenylene-4,4'-diisocyanate, 4,4'-diisocyanate-3,3'-dimethyldiphenyl, 3-methyldiphenyl-methane-4,4'-diisocyanate and diphenyletherdiisocyanate and 2,4,6-triisocyanatotoluene and 2,4,4'-triisocyanatodiphenylether.

Mixtures of isocyanates may be used, such as the commercially available mixtures of 2, 4- and 2, 6-isomers of toluene diisocyantes. TDI/MDI blends may also be used. MDI or TDI based prepolymers made with a polyol can also be used. Isocyanate-terminated prepolymers are prepared by reacting an excess of polyisocyanate with polyols, including aminated polyols or imines/enamines thereof, or polyamines.

Examples of aliphatic polyisocyanates include ethylene diisocyanate, 1,6-hexamethylene diisocyanate (HDI), isophorone diisocyanate (IPDI), cyclohexane 1,4-diisocyanate, 4,4'-dicyclohexylmethane diisocyanate ($H_{12}$MDI), saturated analogues of the above mentioned aromatic isocyanates and mixtures thereof.

The preferred polyisocyanates are the toluene-2, 4- and 2, 6-diisocyanates or MDI or combinations of TDI/MDI or prepolymers made therefrom.

For producing polyurethane foam, a blowing agent is generally required. In the production of flexible polyurethane foams, water is preferred as the blowing agent. The amount of water is preferably in the range of from 0.5 to 10 parts by weight, more preferably from 2 to 7 parts by weight based on 100 parts by weight of the polyol and even more preferably the water is between 2 and 5 parts per hundred parts polyol. In some applications the water is preferably present at 3 parts per hundred or more by weight of the polyol. In some preferred embodiment, the water is present at 6 parts per hundred or less by weight of the polyol. The list of other blowing agents includes liquid or gaseous carbon dioxide, methylene chloride, acetone, pentane, isopentane, cyclopentane, methylal or dimethoxymethane and dimethylcarbonate.

One or more catalysts for the reaction of the polyol with the polyisocyanate can be used. Any suitable urethane catalyst may be used, including tertiary amine compounds, amines with isocyanate reactive groups and organometallic compounds. Exemplary tertiary amine catalysts include triethylenediamine, N-methylmorpholine, N, N-dimethylcyclohexylamine, pentamethyldiethylenetriamine, tetramethylethylenediamine, bis (dimethylaminoethyl) ether, 1-methyl-4-dimethylaminoethyl-piperazine, 3-methoxy-N-dimethylpropylamine, N-ethylmorpholine; dimethylethanolamine, N-cocomorpholine, N, N-dimethyl-N', N'-dimethyl isopropylpropylenediamine, N, N-diethyl-3-diethyl amino-propylamine and dimethylbenzylamine. Exemplary organometallic catalysts include organobismuth, organo mercury, organolead, organoferric and organotin catalysts, with organotin catalysts being preferred among these. Suitable tin catalysts include stannous chloride, tin salts of carboxylic acids such as dibutyltin dilaurate, and stannous octoate, as well as other organometallic compounds. A catalyst for the trimerization of polyisocyanates, resulting in a polyisocyanurate, such as an alkali metal alkoxide may also optionally be employed herein. The amount of amine catalyst can generally vary from 0.02 to 5 percent in the formulation. The amount of organometallic catalyst can generally vary from 0.001 to 1 percent in the formulation.

In making polyurethane foam, it is generally preferred to employ an amount of a surfactant as additive or auxiliary compound to stabilize the foaming reaction mixture until it cures. Such surfactants advantageously comprise a liquid or solid organosilicone surfactant. Other surfactants include polyethylene glycol ethers of long-chain alcohols, tertiary amine or alkanolamine salts of long-chain alkyl acid sulfate esters, alkyl sulfonic esters and alkyl arylsulfonic acids. Such surfactants are employed in amounts sufficient to stabilize the foaming reaction mixture against collapse and the formation of large, uneven cells. Typically, 0.2 to 3 parts of the surfactant per 100 parts by weight total polyol are sufficient for this purpose.

A crosslinking agent or a chain extender may be added as additive or auxiliary compound, if desired. The crosslinking agent or the chain extender includes low-molecular weight polyhydric alcohols such as ethylene glycol, diethylene glycol, 1, 4-butanediol, and glycerol; low-molecular weight amine polyol such as diethanolamine and triethanolamine; polyamines such as ethylene diamine, xylylenediamine, and methylene-bis (o-chloroaniline).

The polyurethane products are either produced continuously or discontinuously, by injection, pouring, spraying, casting and calendaring. These polyurethane products are made under free rise or molded conditions, with or without release agents, in-mold coating, or any inserts or skin put in the mold. In case of flexible foams, the products can be mono- or dual-hardness. Flexible slabstock foam is conveniently prepared by mixing the foam ingredients and dispensing them into a trough or other region where the reaction mixture reacts, rises freely against the atmosphere (sometimes under a film or other flexible covering) and cures. In common commercial scale flexible slabstock foam production, the foam ingredients or various mixtures thereof are pumped independently to a mixing head where they are mixed and dispensed onto a conveyor that is lined with paper or plastic. Foaming and curing occurs on the conveyor to form a foam bun. The resulting foams are typically from about 10 kg/m³ to a maximum of 80 kg/m³. A preferred range is from about 10 kg/m³ to 60 kg/m³ and more preferably from about 10 kg/m³ to 50 kg/m³ in density. In an even more preferred embodiment the flexible slabstock foam has a density of 40 kg/m³ or less.

The polyurethane foams produced according to the present invention can be put into the use in various applications already well known in the industry. Flexible and semi-flexible foams find use in applications such as bedding, furniture, automobile seats, sun visors, armrests, door panels, and noise and heat insulation parts.

EXPERIMENTAL SECTION

General Remarks

Determination of Acid Value:

Approximately 1.00-2.00 grams of sample is added to an Erlenmeyer flask followed by the addition of approximately 75 ml of toluene. The sample is dissolved using a stir bar. The content of the flask may be subjected to heating to dissolve the sample. Once the sample is dissolved, 75 ml of Acid Value Solution is added to the sample flask. The Acid Value Solution is comprised of 600 mL toluene and 300 mL methanol and 3-5 ml of 2% ethanolic phenolphthalein. After the addition of the Acid Value Solution, the resulting solution is titrated with 0.1N methanolic potassium hydroxide (KOH) to a pink end-point. The Acid Value of the samples is calculated from the following formula: Acid Value=[V× N×56.1]/Sample weight (g), where V is the volume in milliliters of KOH solution added and N is the normality of the KOH solution.

Determination of Hydroxyl Value:

An acetic anhydride reagent solution comprising 60 mL acetic anhydride, 7.2 g p-toluenesulfonic acid and 180 mL ethyl acetate and a pyridine-water solution comprising approximately 3 mL pyridine for each mL of water are prepared. Sample weighing 0.75-5.0 g is added to a 250 mL acetylation flask. The amount of samples used in this analysis is dependent on the expected hydroxyl value of the sample. 5 mL of acetic anhydride reagent is added to the sample in the 250 ml acetylation flask and the acetylation flask is attached to an air condenser. A reagent blank with no sample but corresponding volume of the reagents is also prepared in parallel. The acetylation flasks containing the test sample and the reagent blank are incubated at 70-72° C. in a water bath. The acetylation flask containing the test sample is swirled until the solid test sample is melted and thoroughly mixed followed by the incubation of both the flasks at 70-72° C. for one hour. At the end of one hour incubation, the acetylation flasks are removed from water bath and cooled for at least 10 minutes in a room temperature water bath followed by the addition of 2 ml of deionized water and 10 ml of pyridine-water solution to each flask through the air condenser. The flasks are swirled vigorously to achieve through mixing and returned to the 70-72° C. bath for 10 minutes to complete the hydrolysis of the excess acetic anhydride reagent, swirling at frequent intervals. The flasks are removed and cooled in the cooling bath for at least 10 minutes and the condenser is removed. 1 mL of crescol red-thymol blue indicator solution is added and stirred using a magnetic stir bar and the sample and blank are titrated using 0.5N methanolic potassium hydroxide. The end point of the blank is a bold blue color with no trace of red. The end point of the sample depends on the color of the sample, but is usually a deep gray-blue with the disappearance of the last trace of red. Samples should be heated under hot water to release any remaining occluded traces of acid just before the end of the titration. The hydroxyl value is calculated as follows: [(mL KOH blank-mL KOH sample)*N KOH*56.1]/grams sample.

Determination of Functionality of the Hybrid Polyol Preparation.

The functionality of the hybrid polyol prepared according to the present invention is determined theoretically using the functionality value assigned to each of the components that went into the synthesis of hybrid polyol and the relative proportion of each of the component in the final hybrid polyol preparation. The theoretical average functionality can be calculated as seen below:

$$\text{Theoretical Average Functionality} = \frac{\sum eq\ \text{OH} - \sum eq\ \text{acid}}{\sum \text{mol OH} + \sum \text{mol acid} - \sum eq\ \text{acid}}$$

The hydroxyl equivalents (eq OH) are calculated by multiplying the functionality of each polyhydric alcohol by the moles of that polyhydric alcohol in the reaction. Likewise, the acid equivalents (eq acid) are calculated by multiplying the functionality of each polycarboxylic acid by the moles of that polycarboxylic acid in the reaction.

Example 1

Preparation of Hybrid Polyol Using Soybean Derived Natural Oil Polyol, Biobased Succinic Acid and Biobased 1, 3-Propandiol 745 g Agrol® 3.0 (BioBased Technologies, Rogers, Ark. USA), 270 g biobased succinic acid derived from biological fermentation (Myriant Corporation, Woburn, Mass., USA) and 0.63 g Reaxis® C-256 (Reaxis Inc., McDonald, Pa., USA) catalyst was charged in a 3 L round bottom flask under $N_2$ atmosphere. Temperature was set to 210° C., with stirring. 723 g biobased 1, 3-propanediol (Susterra, DuPont Tate & Lyle, Louden, Tenn., USA) was bubbled using the $N_2$ outlet from the reaction vessel. Some sublimation of succinic acid occurred on the top half of the flask. After heating for 3 hours (including warm up time, around 1 hour at 210° C.), the reactor was cooled to 155° C. for addition of 723 g $N_2$-bubbled 1,3-propanediol and 782 g succinic acid. Temperature was set to 80° C. for 1 hour, and a Vigreux column was added to reactor. After 1 hour, temperature was increased in steps over 5 hours to a maximum of 210° C. The vigreux column was then removed, and acid value and hydroxyl value were measured to track reaction progress. A total of 23 g additional 1,3-propanediol was added over 12 hours of cooking at 210° C. to target a theoretical hydroxyl value of 58.9. An additional 0.63 g Reaxis® C-256 was added when the acid value fell below 20. The reaction was cooled when acid value was less than 1. The final acid value was 0.825 mg KOH/g and final hydroxyl value was 57.4 mg KOH/g. A sample of the resulting hybrid polyol was dissolved in tetrahydrofuran (THF) and run on a gel permeation chromatography (GPC). The GPC analysis showed the hybrid polyol prepared according to the method described in this example had a number average molecular weight of 4696, a weight average molecular weight of 14181 and a polydispersity index of 3.02. This batch of hybrid polyol prepared according to the procedure described in this Example is referred as MYR113-88.

Example 2

Preparation of Hybrid Polyol Using Soybean Derived Natural Oil Polyol, Biobased Succinic Acid and Diethylene Glycol 756 g Agrol® 3.0 (BioBased Technologies, Rogers, Ark. USA), 275 g biobased succinic acid derived from biological fermentation (Myriant Corporation, Woburn, Mass., USA) and 0.63 g Reaxis® C-256 catalyst (Reaxis Inc., McDonald, Pa., USA) was charged in a 3 L round bottom flask under $N_2$ atmosphere. Temperature was set to 210° C., with stirring. 853 g diethylene glycol was bubbled using the $N_2$ outlet from the reaction vessel. Some sublimation of succinic acid occurred on the top half of the flask. After heating for 3.5 hours (including warm up time, around 1.5 hour at 210° C.), the reactor was cooled to 155° C. for addition of 853 g $N_2$-bubbled diethylene glycol and 623 g succinic acid. Temperature was set to 80° C. for 1 hour, and a Vigreux column was added to reactor. After 1 hour, the temperature was increased in steps over 8 hours to 210° C. Vigreux column was then removed and measurement of acid value and hydroxyl value was done to track reaction progress. A total of 20 g additional diethylene glycol was added over 24 hours of cooking at 210° C. to target a theoretical hydroxyl value of 58.9. An additional 0.63 g Reaxis® C-256 catalyst was added when the acid value fell below 20. Reaction was cooled when acid value was less than 2. The final acid value of the hybrid polyol preparation was 1.6 mg KOH/g and final hydroxyl value was 54.5 mg KOH/g. This hybrid polyol sample was dissolved in THF and run on a GPC. The GPC analysis revealed that the hybrid polyol prepared according to the method described in this example had a number average molecular weight of 4627, a weight average molecular weight of 14054 and a polydispersity index was 3.03. This batch of hybrid polyol prepared according to the procedure described in this Example is referred as MYR113-121.

Example 3

Preparation of Hybrid Polyol Using Soybean Derived Natural Oil Polyol, Phthalic Anhydride and Bio Based 1, 3-Propanediol 812 g Agrol® 3.0 (BioBased Technologies, Rogers, Ark. USA), 369 g phthalic anhydride, and 0.63 g Reaxis® C-256 catalyst (Reaxis Inc., McDonald, Pa., USA) were charged in a 3 L round bottom flask under $N_2$ atmosphere. Temperature was set to 210° C. After heating for 30 minutes, having reached 130° C., the Vigreux column was added to reactor and 613 g biobased 1,3-propanediol (Susterra, DuPont Tate & Lyle, Louden, Tenn., USA) and 727 g phthalic anhydride were added to the flask. The temperature was set to 100° C. for 1 hour. After 1 hour, the temperature was increased in steps over 4 hours to 205° C. After four hours of incubation at 205° C., the Vigreux column was removed and measurements of acid and hydroxyl values were made to track reaction progress. A total of 27 g additional bio based 1,3-propanediol was added over 30 hours of cooking at 210° C. to target a theoretical hydroxyl value of 58.9. An additional 0.63 g Reaxis® C-256 was added when the acid value fell below 20. The reaction was cooled when acid value was less than 2. The final acid value and hydroxyl value of the resulting hybrid polyol was 1.87 mg KOH/g and 68 mg KOH/g respectively. Viscosity was not measured, but qualitatively this hybrid polyol prepared according to the method described under this example was much more viscous than the hybrid polyols prepared according to the procedures described under Example 1 and Example 2. A sample of resulting hybrid polyol was dissolved in tetrahydrofuran (THF) and run on a gel permeation chromatography (GPC). The GPC analysis showed the hybrid polyol prepared according to the method described in this example had a number average molecular weight of 3769, a weight average molecular weight of 6482 and a polydispersity index of 1.72. This batch of hybrid polyol prepared according to the procedure described in this Example is referred as MYR113-123.

Example 4

Preparation of Hybrid Polyol Using Soybean Derived Natural Oil Polyol, Biobased Succinic Acid and Biobased 1,3-Propanediol 1361.9 g Agrol® 3.0 (BioBased Technologies, Rogers, Ark. USA), 481.7 g biobased succinic acid derived from biological fermentation (Myriant Corporation, Woburn, Mass., USA) and 1.13 g Reaxis® C-256 catalyst (Reaxis Inc., McDonald, Pa., USA) were charged in a 5 L round bottom flask under $N_2$ atmosphere. Temperature was set to 210° C. with stirring. Some sublimation of succinic acid occurred on the top half of the flask and 84 g PDO was added to control sublimation. The contents of the flask were allowed to cook for 6 hours before being cooled overnight. 1190 g biobased 1,3-propanediol (DuPont Tate & Lyle, Louden, Tenn., USA) was bubbled using the $N_2$ outlet from the reaction vessel. 1190 g $N_2$-bubbled 1,3-propanediol (Susterra, DuPont Tate & Lyle, Louden, Tenn., USA) and 1396 g biobased succinic acid derived from biological fermentation (Myriant Corporation, Woburn, Mass., USA) were added to a cooled reactor and temperature was set to 80° C. for 1 hour. A vigreux column was added to reactor. After 1 hour, temperature was increased in steps over 10 hours. The Vigreux column was then removed and measurement of acid and hydroxyl values was carried out to track reaction progress. A total of 84 g 1, 3-propanediol (DuPont Tate & Lyle, Louden, Tenn., USA) was added over 33 hours of cooking at 210° C. to target a theoretical hydroxyl value of 58.4. An additional 1.13 g Reaxis C-256 catalyst (Reaxis Inc., McDonald, Pa., USA) was added when the acid value fell below 20. The reaction was cooled when acid value was less than 1. The final acid value was 0.855 mg KOH/g and final hydroxyl value was 78.8 mg KOH/g. This batch of hybrid polyol prepared according to the procedure described in this Example is referred as MYR113-163.

Example 5

Preparation of Hybrid Polyol Using Soybean Derived Natural Oil Polyol, Biobased Succinic Acid and Diethylene Glycol Charged 1361 g Agrol® 3.0 (BioBased Technologies, Rogers, Ark. USA), 494 g biobased succinic acid derived from biological fermentation (Myriant Corporation, Woburn, Mass., USA) and 1.13 g Reaxis® C-256 catalyst (Reaxis Inc., McDonald, Pa., USA) were charged in a 5 L round bottom flask under $N_2$ atmosphere. Temperature was set to 210° C., with stirring. 1541 g diethylene glycol was bubbled using the N₂ outlet from the reaction vessel. Some sublimation of succinic acid occurred on the top half of the flask. After heating for 6 hours, 1541 g N₂-bubbled diethylene glycol and 1121 g succinic acid derived from biological fermentation (Myriant Corporation, Woburn, Mass., USA) were added. Temperature was set to 80° C. for 1 hour and a vigreux column was added to reactor. Temperature was then increased in steps over 8 hours to 210° C. The Vigreux column was then removed and measurement of acid value and hydroxyl value was done to track reaction progress. A total of 13.6 g diethylene glycol was added over 38 hours of cooking at 210° C. to target a theoretical hydroxyl value of 58.9. An additional 1.13 g Reaxis® C-256 catalyst (Reaxis Inc., McDonald, Pa., USA) was added when the acid value fell below 20. The reaction was cooled when acid value held steady at less than 3. The final acid value was 2.26 mg KOH/g, and the final hydroxyl value was 58.2 mg KOH/g. This batch of hybrid polyol prepared according to the procedure described in this Example is referred as MYR113-172.

Example 6

Preparation of Hybrid Polyol Using Soybean Derived Polyol, Biobased Succinic Acid and Biobased 1,3-Propanediol 1335 g Agrol® 3.0 (BioBased Technologies, Rogers, Ark. USA), 472 g biobased succinic acid derived from biological fermentation (Myriant Corporation, Woburn, Mass., USA), 1.13 g trimethylolpropane, and 1.13 g Reaxis® C-256 catalyst (Reaxis Inc., McDonald, Pa., USA) were charged in a 5 L round bottom flask under N₂ atmosphere. The temperature was set to 210° C., with stirring. Some sublimation of succinic acid occurred on the top half of the flask. 75 g 1,3-propanediol (DuPont Tate & Lyle, Louden, Tenn., USA) was added after 3 hours at temperature to control succinic acid sublimation. 1170 g 1,3-propanediol (DuPont Tate & Lyle, Louden, Tenn., USA) was bubbled using the N₂ outlet from the reaction vessel. After heating for 5 hours, acid value was analyzed to be AV=104 and 1170 g N₂-bubbled 1,3-propanediol (Susterra, DuPont Tate & Lyle, Louden, Tenn., USA), 103.4 g trimethylolpropane, and 1370 g biobased succinic acid derived from biological fermentation (Myriant Corporation, Woburn, Mass., USA) was added. Temperature was set to 90° C. for 1 hour and a vigreux column was added to reactor. After 1 hour hold time, temperature was increased in steps over 8 hours. Vigreux column was then removed and acid value and hydroxyl value testing was done to track reaction progress, targeting a theoretical hydroxyl value of 84.6. An additional 1.13 g Reaxis® C-256 catalyst (Reaxis Inc., McDonald, Pa., USA) was added when the acid value fell below 20. The reaction was cooled when acid value was less than 1. The final acid value was 0.95 mg KOH/g and final hydroxyl value was 80.5 mg KOH/g. This batch of hybrid polyol prepared according to the procedure described in this Example is referred as MYR160-9.

Example 7

Preparation of Hybrid Polyol Using Bean Derived Natural Oil Polyol, Bio Based Succinic Acid and Bio Based 1,3-Propanediol 741.6 g Agrol® 3.0 (BioBased Technologies, Rogers, Ark. USA), 262.3 g biobased succinic acid derived from biological fermentation (Myriant Corporation, Woburn, Mass., USA) and 0.63 g titanium (IV) isopropoxide (Sigma Aldrich) were charged in a 3 L round bottom flask under N₂ atmosphere. Temperature was set to 80° C. with stirring for 1 hour, then temperature was increased to 205° C. Some sublimation of succinic acid occurred on the top half of the flask and 42.8 g PDO was added to control sublimation and a vigreux column was added. The contents of the flask were reacted for 7 hours. The reactor was cooled to 150° C. and 646 g 1,3-propanediol (Susterra, DuPont Tate & Lyle, Louden, Tenn., USA), 760 g succinic acid derived from biological fermentation (Myriant Corporation, Woburn, Mass., USA), and 58.1 g trimethylolpropane (Alfa Aesar) were added. Temperature was increased in steps over 10 hours to a maximum of 205° C. Then, the vigreux column was then removed and measurement of acid value was carried out to track reaction progress. An additional 0.63 g titanium (IV) isopropoxide (Sigma Aldrich) was added when the acid value fell below 20. The reaction was cooled when acid value was less than 1. The final acid value was 0.67 mg KOH/g and the final hydroxyl value was 68.7 mg KOH/g. This batch of hybrid polyol prepared according to the procedure described in this Example is referred as MYR160-69.

Example 8

Preparation of Biobased Polyester Polyol Comprising Biobased Isosorbide, Biobased Succinic Acid and Biobased 1,3 Propanediol A biobased polyester polyol comprising biobased isosorbide, biobased succinic acid and biobased 1,3 propanediol was prepared by adding 680 grams of biobased isosorbide (Polysorb PA, Roquette, Lestrem, France), 124.6 grams of trimethylolpropane (Alfa Aesar), 127 grams of biobased 1,3 propanediol (DuPont Tate & Lyle, Louden, Tenn., USA), 1097 grams of biobased succinic acid derived from biological fermentation (Myriant Corporation, Woburn, Mass., USA), 5.16 grams Anox® 1315 (Addivant, Danbury, Conn., USA), and 0.38 grams of Reaxis® C-256 (Reaxis Inc., McDonald, Pa., USA) under nitrogen and heating the mixture to 80° C. The reaction was held at 80° C. for 1 hour, then the temperature was increased to 210° C. After approximately 9 hours, an additional 500 grams of 1,3 propanediol (DuPont Tate & Lyle, Louden, Tenn., USA) was added to the reaction, and the temperature gradually increased to 205° C. When the acid value fell below 20, an additional 0.38 grams of Reaxis® C-256 (Reaxis Inc., McDonald, Pa., USA) were added and the reaction was held at 205° C. until the acid value was less than 1. The final measured acid value of this polyester polyol preparation was 0.87 mg KOH/g. This batch of polyester polyol prepared according to the procedure described in this Example is referred as 51701251. The presence of isosorbide in the polyurethane formulation adds rigidity, strength and toughness.

Example 9

Preparation and Testing of Polyurethane Foams

A plywood box with an internal dimensions (L×B×H) of about 12"×7"×7" was constructed and a grocery bag was cut to size to fit inside the box and taped to the inside. The plywood box helps the foam sample to maintain a rectangular shape which makes cutting the foam sample easier.

A calibrated balance, located in the fume hood, was used for weighing all materials. All the polyols and the additives with the exclusion of the isocyanate were weighed into beaker A. Toluene diisocyanate (TDI) was measured into beaker B using the "wet tare" technique. The wet tare technique compensates for any hold-up in the beaker during the pouring process and the wet tare technique involves step of filling the beaker and emptying the contents once before setting the zero point on the scale.

The components in beaker A were mixed for 10 seconds (using a traceable timer). At the 10 second point, the isocyanate was added to beaker A from beaker B. At 20 seconds on the timer or just before cream time, the foaming mixture was poured into the box. All mixing was done using a drill mixer attached to a stand. The drill mixer has a speed of about 1500 RPM.

Common observations of the foam mixture are the cream time (when the mixture goes from a translucent liquid to a creamy state), the rise time (the moment when the foaming mass stops rising) and time to the appearance of healthy bubbles at the surface of the foam at approximately the time of full rise, which signifies a proper reaction balance.

A polyurethane formulation was prepared containing only petrochemical derived polyether polyol Carpenter Carbopol GP 3008 using the composition shown in Table 1. Carpenter Carbopol GP 3008 is a 3000 MW glycerol and propylene oxide based polyether polyol triol with 8% ethylene oxide located internally. Carpenter Carbopol GP 3008 is suitable for flexible slabstock polyurethane foam. The polyurethane formulation prepared using only the polyether polyol Carpenter Carbopol GP 3008 is described in this invention is referred as "Control" or "Control Formulation" or "Control Polyurethane Formulation". The relative fraction of various components in the Control Polyurethane Formulation in Table 1 are represent by the term pph (parts per hundred on a weight basis).

A number of polyurethane foam batches comprising petrochemical derived polyether polyol and different percentage of biobased hybrid polyols were prepared using the composition as shown in the Tables 2 and 3. The contribution of hybrid polyol prepared according to the invention is indicated by the term "parts per hundred" (pph). Thus when the content of hybrid polyol content in the final polyurethane preparation is indicated by 25 pph, in the final polyurethane preparation, twenty five percent of polyol content is represented by specified hybrid polyol prepared according to the present invention. Since certain hybrid polyols prepared according to the present invention such as the Batch MYR113-163 are prepared using entirely biobased components, the contribution of the biobased component in the total polyol used in the preparation of 113-163 (25 pph) polyurethane can be considered as 25%. In other words, the polyurethane prepared using 25 pph of MYR113-163 batch of hybrid polyol contains 25% renewable bio based materials. As indicated in the Example 4, the MYR113-163 batch of the hybrid polyol was prepared using Agrol® 3.0, succinic acid and 1,3-propanediol all of which are derived from biobased materials. The hybrid polyol Batch 113-163 and Batch 113-172 used in the preparation of polyurethane formulations with biobased component as shown in the Table 2 had hydroxyl value of 78.8 mg KOH/g and 58.2 mg KOH/g respectively. The hybrid polyol Batch 160-9 used in the preparation of polyurethane formulations with biobased component as shown in the Table 3 had hydroxyl value of 80.5 mg KOH/g.

The testing of physical properties of various foam formulations prepared using the different proportion of hybrid polyols was carried in accordance to ASTM 3574-11 method which is widely used in the industry. The list of the physical properties of various foam formulations tested in the present invention includes density, Compression Force Deflection (CFD) 25% and 65% (foam hardness), Tensile strength, Elongation at Break, Resiliency (Ball Rebound), Air Flow Resistance, Compression Set and Wet Compression Set. The results of physical testing are provide in the Table 4-13.

Figure 6:
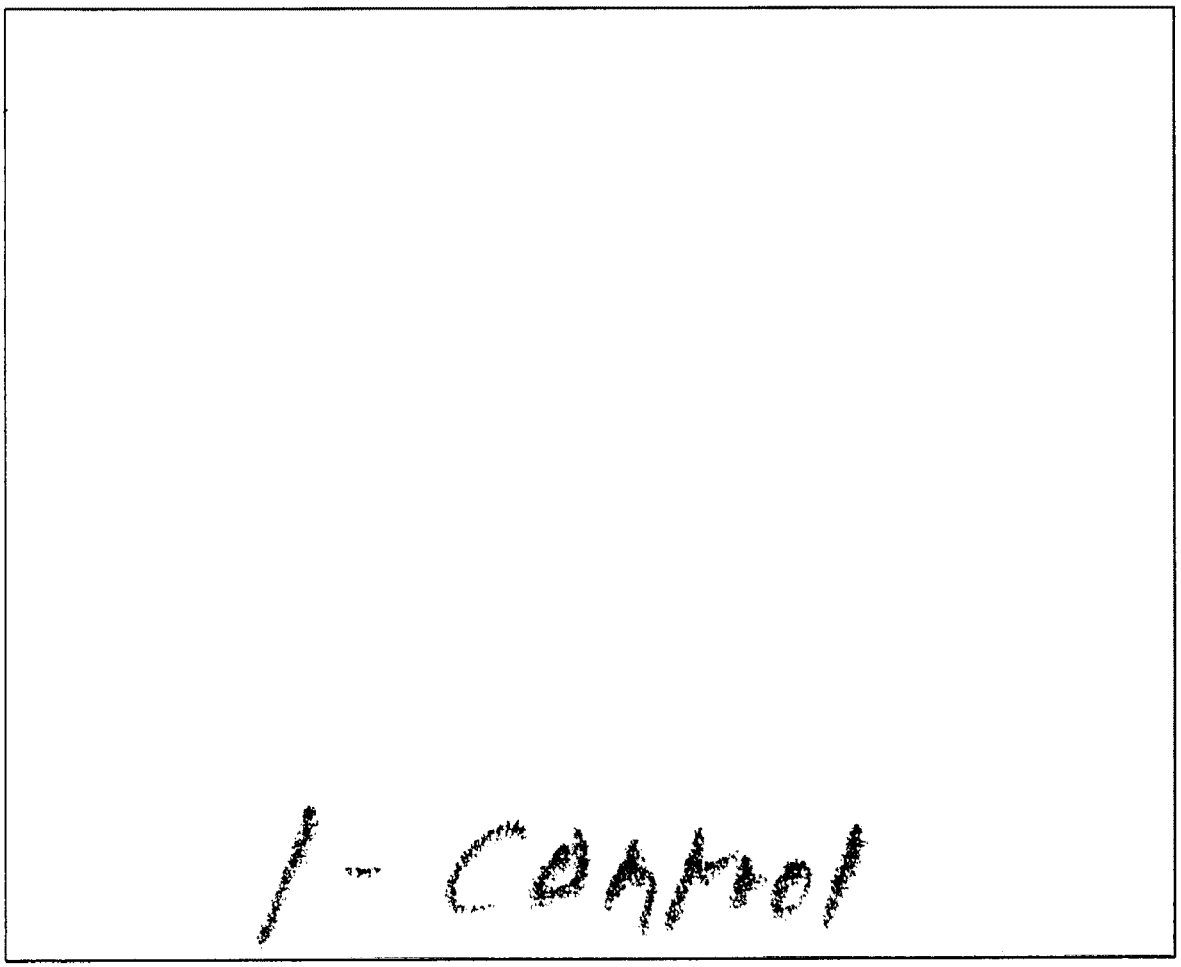
FIG. 6. Physical appearance of the flexible polyurethane foam formulation prepared using the petrochemical derived polyether polyol.
Figure 7:
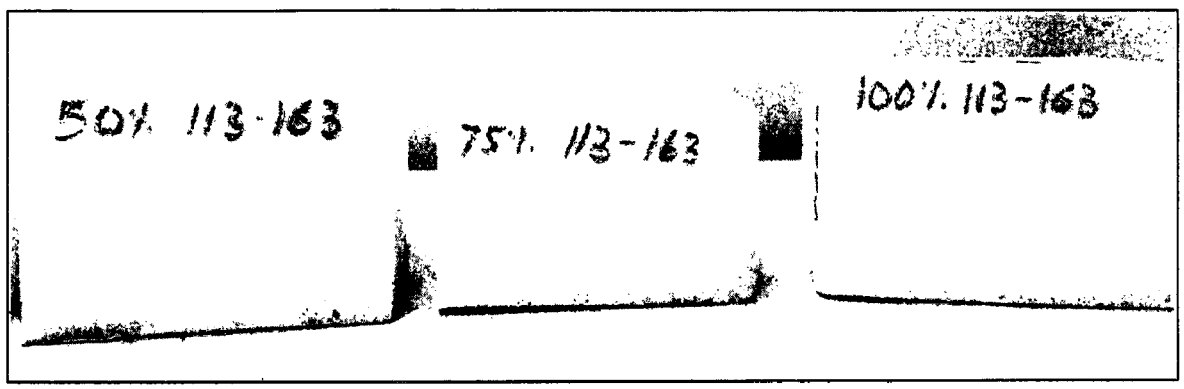
FIG. 7. Physical appearance of the flexible polyurethane foam formulations prepared using a polyol mixture comprising petrochemical derived polyether polyol and biobased hybrid polyol Batch No. MYR113-163 at 50% (v/v), or 75% (v/v) and the flexible polyurethane foam formulations prepared using 100% (v/v) of biobased hybrid polyol Batch No. MYR113-163. Since MYR113-163 was prepared using the biobased natural oil polyol Agrol®, biobased succinic acid and biobased 1, 3-propanediol, this hybrid polyol is almost 100% biobased. In the preparation of the flexible polyurethane foam labelled "50% 113-163", polyol mixture comprising 50% (v/v) polyether polyol from petrochemical source and 50% (v/v) hybrid polyol Batch No. MYR113-163 were mixed together and used. The resulting flexible polyurethane foam preparation is calculated to have 50% biobased content. In the preparation of the flexible polyurethane foam labelled "75% 113-163", polyol mixture comprising 25% (v/v) polyether polyol from petrochemical source and 75% (v/v) hybrid polyol Batch No. MYR113-163 were mixed together and used. The resulting flexible polyurethane foam preparation is calculated to have 75% biobased content. In the preparation of the flexible polyurethane foam labelled "100% 113-163", only the hybrid polyol Batch No. MYR113-163 was used. The resulting flexible polyurethane foam preparation is calculated to have 100% biobased content.
Figure 8:
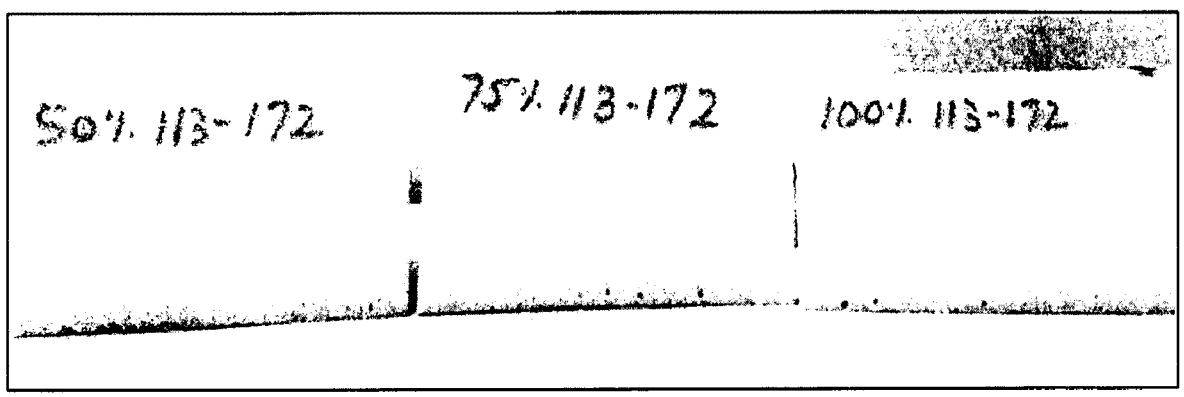
FIG. 8. Physical appearance of the flexible polyurethane foam formulations prepared using a polyol mixture comprising petrochemical derived polyether polyol and biobased hybrid polyol Batch No. MYR113-172 at 50% (v/v), or 75% (v/v) and the flexible polyurethane foam formulations prepared using 100% (v/v) of hybrid polyol Batch No. MYR113-172. Since the hybrid polyol Batch No. MYR113-172 was prepared using the biobased natural oil polyol Agrol®, biobased succinic acid and diethylene glycol, the biobased content of this hybrid polyol is proportional to the content of the biobased natural oil polyol Agrol® and biobased succinic acid. In the preparation of the flexible polyurethane foam labelled "50% 113-172", polyol mixture comprising 50% (v/v) polyether polyol from petrochemical source and 50% (v/v) hybrid polyol Batch No. MYR113-172 were mixed together and used. In the preparation of the flexible polyurethane foam labelled "75% 113-172", polyol mixture comprising 25% (v/v) polyether polyol from petrochemical source and 75% (v/v) hybrid polyol Batch No. MYR113-172 were mixed together and used. In the preparation of the flexible polyurethane foam labelled "100% 113-172", only the hybrid polyol Batch No. MYR113-172 was used.

Physical appearance of the control polyurethane formulation and the polyurethane formulations comprising increasing fraction of biobased component are illustrated in FIGS. 6, 7 and 8. As illustrated in these figures, in term of physical appearance, there is no difference at all between the control polyurethane formulation and various other formulations with increasing bio based content prepared according to the present invention. All of the foams were generally of acceptable quality, although it clearly became lower in air-flow as the levels of the experimental polyols were increased. To compensate for this effect, foams were made with hybrid polyol MYR113-163 using lower tin catalyst level to raise the air-flow as indicated in the Table 2.

Example 10

Preparation and Testing of Polyurethane Foams Using Bio Based Co-Polyester Polyol Comprising Isosorbide, Succinic Acid and 1,3 Propanediol In preparing a polyurethane foam comprising biobased polyester polyol comprising isosorbide, succinic acid and 1,3 propandiol, 885 grams (85%) of MYR160-69 prepared as in the Example 7 was mixed with 156 grams (15%) of 51701251 prepared as in the Example 8 to yield the composition MYR160-98 (Table 14). A polyurethane foam preparation was formulated by combining the reagents as in the Table 15. A total of five different foam formulations were prepared with increasing concentration of MYR160-98 from 0% to 50. The testing of physical properties of these various foam formulations was carried in accordance to ASTM 3574-11 method which is widely used in the industry. The list of the physical properties of various foam formulations tested in the present invention includes density, Frazier Perm (½"), Compression Force Deflection (CFD) 25% and 65% (foam hardness), Tensile strength, Elongation at Break, Resiliency (Ball Rebound), Air Flow Resistance, 50% and 90% Compression Set and Wet Compression Set. The results of physical testing are provide in the Table 16.

TABLE 1

Composition of control formulation prepared with petrochemical derived components

| Reagent | Source | pph |
| --- | --- | --- |
| Base Polyol (OH# = 56) | Carpenter GP3008 | 100 |
| Surfactant | Tegostab B8244 | 1 |
| Blow reaction catalyst | Jeffcat ZF-10 | 0.12 |
| Balanced reaction catalyst | Jeffcat LE-210 | 0.18 |
| Gel Catalyst | Kosmos 29 | 0.2 |
| Water | | 3.8 |
| Toluene Diisocyanate | TD-80 | 48.22 |
| Isocyanate Index | | 106 |

TABLE 2

Summary of Polyurethane Formulations with Biorenewable Component

| Identity | No | TDI Level (pph) | Tin Catalyst (pph) | Cream Time (seconds) | Rise Time (seconds) | Health Bubbles |
|---|---|---|---|---|---|---|
| Control | 1 | 48.22 | 0.20 | 23 | 101 | Yes |
| 113-163 (OH # 78.8) (25 pph) | 2 | 49.08 | 0.20 | 21 | 100 | Yes |
| 113-163 (OH# 78.8) (25 pph) | 2C | 49.08 | 0.08 | 25 | 143 | Yes |
| 113-163 (OH#78.8) (50 pph) | 3 | 50.01 | 0.20 | 20 | 98 | Yes |
| 113-163 (OH #78.8) (50 pph) | 3C | 50.01 | 0.08 | 24 | 138 | Yes |
| 113-163 (OH#78.8) (75 pph) | 4 | 50.95 | 0.20 | 19 | 99 | Yes |
| 113-163 (OH#78.8) (75 pph) | 4C | 50.95 | 0.10 | 23 | 140 | Yes |
| 113-163 (OH#78.8) (100 pph) | 5 | 51.89 | 0.20 | 24 | 111 | Yes |
| 113-163 (OH#78.8) (100 pph) | 5B | 51.89 | 0.05 | 25 | 131 | Yes |
| 113-172 (OH#58.2) (25 pph) | 6 | 48.23 | 0.06 | 22 | 104 | Yes |
| 113-172 (OH#58.2) (50 pph) | 7 | 48.32 | 0.06 | 21 | 103 | Yes |
| 113-172 (OH#58.2) (75 pph) | 8 | 48.41 | 0.2 | 20 | 100 | Yes |
| 113-172 (OH#58.2) (100 pph) | 9 | 48.50 | 0.2 | 19 | 98 | Yes |

TABLE 3

Summary of Polyurethane Formulations with Biorenewable Component

| Identity | No | TDI Level (pph) | Tin Catalyst (pph) | Cream Time (seconds) | Rise Time (seconds) | Health Bubbles | % of Air Flow Scale |
|---|---|---|---|---|---|---|---|
| Control | 1 | 48.22 | 0.20 | 23 | 101 | Yes | 75 |
| 160-9 (OH # 80) (10 pph) | 2 | 48.61 | 0.18 | 21 | 100 | Yes | 75 |
| 160-9 (OH# 80) (25 pph) | 3 | 49.19 | 0.15 | 20 | 98 | Yes | 74 |
| 160-9 (OH# 80) (50 pph) | 4 | 50.15 | 0.10 | 19 | 99 | Yes | 68 |
| 160-9 (OH# 80) (75 pph) | 5 | 51.12 | 0.08 | 23 | 140 | Yes | 35 |
| 160-9 (OH# 80) (100 pph) | 6 | 52.09 | 0.05 | 24 | 111 | Yes | 30 |

TABLE 4

Summary of Physical properties of the polyurethane foams with biorenewable content

| Sample Description | Sample ID | Density | Air flow (% Scale) | Coin-set 50% | Wet Set 50% | Ball Rebound (%) | Tear (lb/in) | Tensile (psi) | Elongation (%) | 25% CFD (psi) | 65% CFD (psi) |
|---|---|---|---|---|---|---|---|---|---|---|---|
| Control | 1 | 1.68 | 75 | 1.61 | 8.58 | 40 | 2.68 | 13.79 | 338.10 | 0.34 | 0.58 |
| 25% 113-163 | 2 | 1.67 | 65 | 6.02 | 13.83 | 32 | 2.41 | 12.59 | 308.02 | 0.33 | 0.53 |
| 25% 113-163 | 2C | 1.68 | 77 | 6.27 | 11.42 | 34 | 1.97 | 11.22 | 275.74 | 0.29 | 0.51 |
| 25% 113-163 | 3 | 1.69 | 50 | 9.04 | 36.52 | 22 | 1.85 | 12.97 | 271.10 | 0.237 | 0.61 |
| 25% 113-163 | 3C | 1.68 | 75 | 13.55 | 26.8 | 28 | 2.00 | 11.82 | 273.47 | 0.28 | 0.48 |
| 25% 113-163 | 4 | 1.7 | 33 | 27.99 | 42.04 | 15 | 1.65 | 12.98 | 246.51 | 0.40 | 0.68 |
| 25% 113-163 | 4C | 1.7 | 72 | 11.77 | 31.76 | 22 | 1.71 | 9.17 | 206.77 | 0.24 | 0.44 |
| 25% 113-163 | 5 | 1.89 | 35 | 32.97 | 44.78 | 20 | 1.30 | 10.72 | 198.69 | 0.37 | 0.66 |
| 25% 113-163 | 5B | 1.87 | 72 | 43.59 | 40.93 | 16 | 1.05 | 8.67 | 190.06 | 0.32 | 0.63 |
| 25% 113-172 | 6 | 1.67 | 55 | 7.18 | 19.08 | 24 | 2.22 | 13.35 | 313.73 | 0.39 | 0.64 |
| 50% 113-172 | 7 | 1.64 | 39 | 8.71 | 36.42 | 20 | 2.16 | 11.38 | 277.96 | 0.28 | 0.48 |
| 75% 113-172 | 8 | 1.63 | 32 | 13.85 | 38.71 | 18 | 1.58 | 9.49 | 227.30 | 0.36 | 0.57 |
| 100 113-172 | 9 | 1.79 | 26 | 30.01 | 47.02 | 12 | 1.19 | 8.79 | 185.61 | 0.38 | 0.65 |

TABLE 5

Summary of Physical properties of the polyurethane foams with biorenwable content

| Sample ID | Density (pcf) | Dry Com-set 50% | Wet Set 50% | Dry Com-Set 90% | Ball Rebound (%) | Tear (lb/in) | Tensile (psi) | Elongation (%) | 25% CFD (psi) | 65% CFD (psi) |
|---|---|---|---|---|---|---|---|---|---|---|
| Control | 1.66 | 2.6 | 6.3 | 4.6 | 38 | 2.5 | 13.5 | 341 | 0.28 | 0.44 |
| 10% 160-9 | 1.62 | 2.9 | 7.1 | 3.8 | 34 | 2.2 | 11.9 | 296 | 0.29 | 0.46 |

TABLE 5-continued

Summary of Physical properties of the polyurethane foams with biorenewable content

| Sample ID | Density (pcf) | Dry Com-set 50% | Wet Set 50% | Dry Com-Set 90% | Ball Rebound (%) | Tear (lb/in) | Tensile (psi) | Elongation (%) | 25% CFD (psi) | 65% CFD (psi) |
|---|---|---|---|---|---|---|---|---|---|---|
| 25% 160-9 | 1.61 | 3.2 | 10.4 | 8.4 | 34 | 2.3 | 11.2 | 267 | 0.28 | 0.47 |
| 50% 160-9 | 1.65 | 6.7 | 18.4 | 12.7 | 26 | 1.6 | 12.2 | 198 | 0.34 | 0.57 |
| 75% 160-9 | 1.78 | 14.3 | 34.0 | 75.5 | 16 | 1.4 | 11.8 | 175 | 0.35 | 0.60 |
| 100% 160-9 | 2 | 22.5 | 35.6 | 69.7 | 14 | 1.3 | 12.0 | 175 | 0.39 | 0.72 |

TABLE 6

Density values for polyurethane preparations containing different proportions of biorenewable content.

| Sample | Density (pcf) | | | | |
|---|---|---|---|---|---|
| Percentage of Bio Renewable Component | 10% | 25% | 50% | 75% | 100% |
| Version 1 (113-163 Low Sn Catalyst) | 1.68 | 1.68 | 1.68 | 1.7 | 1.87 |
| Version 2 (160-9) | 1.62 | 1.61 | 1.65 | 1.78 | 2.0 |
| Version 3 (113-172) | | 1.67 | 1.64 | 1.63 | 1.79 |

TABLE 7

Hardness values for polyurethane preparations containing different proportions of biorenewable content.

| Sample | Hardness (CFD 25%) (psi) | | | |
|---|---|---|---|---|
| Percentage of Bio Renewable Component | 25% | 50% | 75% | 100% |
| Version 1 (113-163 Low Sn Catalyst) | 0.29 | 0.28 | 0.24 | 0.32 |
| Version 2 (160-9) | 0.29 | 0.34 | 0.35 | 0.39 |
| Version 3 (113-172) | 0.33 | 0.37 | 0.36 | 0.38 |

TABLE 8

Ball Rebound values for polyurethane preparations containing different proportions of biorenewable content.

| Sample | Ball Rebound (% of scale) | | | |
|---|---|---|---|---|
| Percentage of Bio Renewable Component | 25% | 50% | 75% | 100% |
| Version 1 (113-163 Low Sn Catalyst) | 34 | 28 | 22 | 16 |
| Version 2 (160-9) | 34 | 26 | 16 | 14 |
| Version 3 (113-172) | 24 | 20 | 18 | 12 |

TABLE 9

Compression Set (50%) values for polyurethane preparations containing different proportions of biorenewable content.

| Sample | Compression Set (50%) | | | |
|---|---|---|---|---|
| Percentage of Bio Renewable Component | 25% | 50% | 75% | 100% |
| Version 1 (113-163 Low Sn Catalyst) | 6.27 | 13.55 | 11.77 | 43.59 |
| Version 2 (160-9) | 3.24 | 6.74 | 14.3 | 22.53 |
| Version 3 (113-172) | 7.18 | 8.71 | 13.85 | 30.01 |

TABLE 10

Tear strength values for polyurethane preparations containing different proportions of biorenewable content.

| Sample | Tear Strength (pli) | | | |
|---|---|---|---|---|
| Percentage of Bio Renewable Component | 25% | 50% | 75% | 100% |
| Version 1 (113-163 Low Sn Catalyst) | 1.97 | 2 | 1.71 | 1.05 |
| Version 2 (160-9) | 2.28 | 1.63 | 1.38 | 1.28 |
| Version 3 (113-172) | 2.22 | 2.16 | 1.58 | 1.19 |

TABLE 11

Tensile strength values for polyurethane preparations containing different proportions of biorenewable content.

| Sample | Tensile Strength (psi) | | | |
|---|---|---|---|---|
| Percentage of Bio Renewable Component | 25% | 50% | 75% | 100% |
| Version 1 (113-163 Low Sn Catalyst) | 11.22 | 11.82 | 9.17 | 8.67 |
| Version 2 (160-9) | 11.15 | 12.16 | 11.77 | 12.02 |
| Version 3 (113-172) | 13.35 | 11.38 | 9.49 | 8.79 |

TABLE 12

Elongation values for polyurethane preparations containing different proportions of biorenewable content.

| Sample | Elongation (%) | | | |
|---|---|---|---|---|
| Percentage of Bio Renewable Component | 25% | 50% | 75% | 100% |
| Version 1 (113-163 Low Sn Catalyst) | 276 | 273 | 207 | 190 |
| Version 2 (160-9) | 267 | 198 | 175 | 175 |
| Version 3 (113-172) | 314 | 278 | 227.3 | 185.61 |

TABLE 13

Wet Compression Set values for polyurethane preparations containing different proportions of biorenewable content.

| Sample | Wet Compression Set (50%) | | | |
|---|---|---|---|---|
| Percentage of Bio Renewable Component | 25% | 50% | 75% | 100% |
| Version 1 (113-163 Low Sn Catalyst) | 11.42 | 26.8 | 31.76 | 40.93 |
| Version 2 (160-9) | 10.35 | 18.4 | 34.02 | 35.61 |
| Version 3 (113-172) | 19.08 | 36.42 | 38.71 | 47.02 |

TABLE 14

Composition of MYR 160-98

| Component | Percent |
|---|---|
| MYR 160-69, 885 g | 85% |
| 51701251, 156 g | 15% |

TABLE 15

Blended mixture for foam synthesis in evaluation of MYR 160-98

| | |
|---|---|
| CP3008 (~3000 MW Polyether Triol) | 100 - x |
| Myr 160-98 (Experimental Polyol) | x |
| B8244 (Surfactant) | 1 |
| ZF-10 (Amine Catalyst - Blow) | 0.12 |
| LE-210 (Amine Catalyst - Balanced) | 0.18 |
| Kosmos 29 (GEL) | y |
| Water | 3.8 |
| TDI80 | z |

TABLE 16

Properties of Foam Preparation MYR 160-98

| Sample/Property | Control | 15 pph | 25 pph | 35 pph | 50 pph |
|---|---|---|---|---|---|
| Density - pcf | 1.71 | 1.77 | 1.83 | 1.87 | 1.93 |
| Frazier Perm ft/min | 272 | 191 | 206 | 248 | 201 |
| CFD 25% | 0.32 | 0.45 | 0.37 | 0.32 | 0.33 |
| CFD 65% | 0.54 | 0.72 | 0.61 | 0.6 | 0.6 |
| Suport factor | 1.69 | 1.60 | 1.65 | 1.88 | 1.82 |
| Ball Rebound | 30 | 30 | 30 | 28 | 25 |
| Tear | 2.61 | 2.61 | 2.67 | 2.39 | 2.3 |
| Tensile | 13.3 | 16.4 | 15.1 | 16.6 | 17.0 |
| Elongation | 298 | 294.7 | 276 | 237.5 | 239 |
| 50% Comp Set | 3.7 | 5.3 | 4.3 | 12.7 | 22.1 |
| 90% Comp Set | 9.6 | 10.2 | 10.2 | 27.9 | 83.1 |
| Tin Catalyst Level (pph) | 0.2 | | 0.17 | 0.15 | 0.05 |
| TD180 (pph) "z" | 48.22 | 49.1 | 49.74 | 50.37 | 51.33 |
| Health Bubbles | YES | YES | YES | YES | YES |
| Cream time (sec) | 19 | 22 | 23 | 24 | 26 |
| Rise time (sec) | 110 | 123 | 113 | 143 | 151 |

REFERENCES

All the patent documents cited herein are incorporated by reference in entirety.

U.S. Pat. No. 2,968,575
U.S. Pat. No. 3,036,042
U.S. Pat. No. 3,479,310
U.S. Pat. No. 4,534,907
U.S. Pat. No. 4,640,801
U.S. Pat. No. 4,714,717
U.S. Pat. No. 6,107,433
U.S. Pat. No. 6,121,398
U.S. Pat. No. 6,291,409
U.S. Pat. No. 6,433,121
U.S. Pat. No. 6,897,283
U.S. Pat. No. 6,962,636
U.S. Pat. No. 6,979,477
U.S. Pat. No. 8,153,746
U.S. Pat. No. 8,293,808
U.S. Pat. No. 8,541,536
U.S. Pat. No. 8,507,701
U.S. Pat. No. 8,575,294
U.S. Pat. No. 8,664,352
U.S. Pat. No. 8,692,030
U.S. Pat. No. 8,765,828
U.S. Pat. No. 8,828,269
U.S. Pat. No. 9,212,250
U.S. Pat. No. 9,260,346
U.S. Patent Application Publication No. US 2006/0276609
U.S. Patent Application Publication No. US 2010/0104872
U.S. Patent Application Publication No. US 2010/0298453
U.S. Patent Application Publication No. US 2012/0022186
U.S. Patent Application Publication No. US 2012/0277338
U.S. Patent Application Publication No. US 2013/0035467
U.S. Patent Application Publication No. US 2016/0002386
International Patent Application Publication No. WO 2003/029182
International Patent Application Publication No. WO 2004/020497
International Patent Application Publication No. WO 2004/096744
International Patent Application Publication No. WO 2009/045926
International Patent Application Publication No. WO 2011/137011
International Patent Application Publication No. WO 2013/053555
International Patent Application Publication No. WO 2015/047919
Desroches, M., Escouvois, M., Auvergne, R., Caillol, S. and Boutevin, B. (2012) from vegetable oils to polyurethanes: Synthetic routes to polyls and main industrial products. Polymer Reviews 52: 38-79.

Miao, S., Wang, P., Su, Z and Zhang, S. (2014) Vegetable-oli-based polymers as future polymeric biomaterials. Acta Bomaterialia 10: 1692-1704.

Patel, M. R., Shukla, J. M., Patel, N. K. and Patel, K. H. (2009) Biomaterials based novel polyurethane adhesion for wood to wood and metal to metal binding. Materials Research, 12: 385-393.

Petrovic, Z. S., Javani, I., Jing, X., Hong, D. P. and Guo, A. (2007) Effect of hyperbranched vegetable oil polyols on properties of flexible polyurethane foams. Materials Sci. Forum. 555: 459-465.

Petrovic, Z. S., Cvetkovic, I., Hong, D., Wan, X. Zhang, W., Abraham, T. W. and M alsam, J. (2010) Vegetable oil-based triols from hydrofomylated fatty acid and polyurethane elastomers. Eur. J. Lipd Sci. Technol. 112: 97-102.

Petrovic, Z. S., Ji, Ye, Inoescu, M. (2010) Polyurethanes from hybrid vegetable oil/petrochemical polyester polyols. Polymer Preprints 51: 757-758.

Petrovic, Z. S., Javni, I. and Ionescu, M. (2013) Biological oils as precursors to novel polymeric materials. J. Renew. Mater. 1: 167-186.

Raquez, J.-M., Deleglise, M., Lacrampe, M.-F. and Krawczak, P. (2010) Thermosetting (bio)materials derived from renewable resources: A critical review. Progress in Polymer Science 35: 487-509.

Zlatanic, A., Javani, I., Lonescu, M., Bilic, N. and Pterovic, Z. S. (2015) Polyurethane molded foams with high content of hyperbranched polyls from soybean oil. J. Cellular Plastics, 51: 289-306.

What is claimed:

1. A hybrid polyol, comprising, in reacted form:
a functionalized natural oil or natural oil polyol useful in flexible polyurethane foam manufacturing; and
a bio-based polyester polyol comprising, in polyesterified form, a polyfunctional carboxylic acid and a polyhydric alcohol, grafted onto the functionalized natural oil or natural oil polyol,
wherein the functionalized natural oil or natural oil polyol is derived from one or more triglycerides comprising a fatty acid side chain in place of introducing functionality comprising 12 to 22 carbon atoms, and
wherein the hybrid polyol has an average functionality in a range of from 0.2 to 4.0 and a hydroxyl number in a range of from 30 to 250.

2. The hybrid polyol of claim 1, wherein the functionalized natural oil or natural oil polyol is prepared from a natural oil selected from a group consisting of castor oil, coconut oil, cochin oil, corn oil, cottonseed oil, linseed oil, olive oil, palm oil, palm kernel oil, peanut oil, soybean oil, sunflower oil, tall oils, tallow, *lesquerella* oil, tung oil, whale oil, tea seed oil, sesame seed oil, safflower oil, rapeseed oil, fish oils, any derivatives thereof, and any combinations thereof,
wherein the polyfunctional carboxylic acid is selected from a group consisting of succinic acid, oxalic acid, malonic acid, maleic acid, fumaric acid, glutaric acid, adipic acid, pimelic acid, suberic acid, azelaic acid, citraconic acid, sebacic acid, fumaric acid, malic acid, itaconic acid, muconic acid, citric acid, phthalic acid, isophthalic acid, aconitic acid, propane-1,2,3-tricarboxylic acid, trimesic acid, 2-butynedioic acid, 1,4-cyclohexane dicarboxylic acid, hexahydrophthalic acid, hexachloroendomethylenetetrahydrophthalic acid, dichlorophthalic acid, isophthalic acid, terephthalic acid, trimellitic acid, any derivatives thereof, and any combination thereof, and
wherein the polyhydric alcohol is selected from a group consisting of ethylene glycol, propylene glycol, neopentylglycol, butanediol, pentanediol, hexanediol, cyclopentanediol, cyclohexanediol, dimethylol cyclohexane, diethylene glycol, glycerol, trimethylolpropane, butanetriol, pentaerytritol, dipentaeiythritol, cyclohexanetriol, 1,3-propanediol, 1,4-butanediol, any mixture thereof, any derivatives thereof, and any combinations thereof.

3. The hybrid polyol of claim 1, wherein the polyfunctional carboxylic acid is succinic acid,
wherein the polyhydric alcohol is diethylene glycol,
wherein the functionalized natural oil has a structure (i)

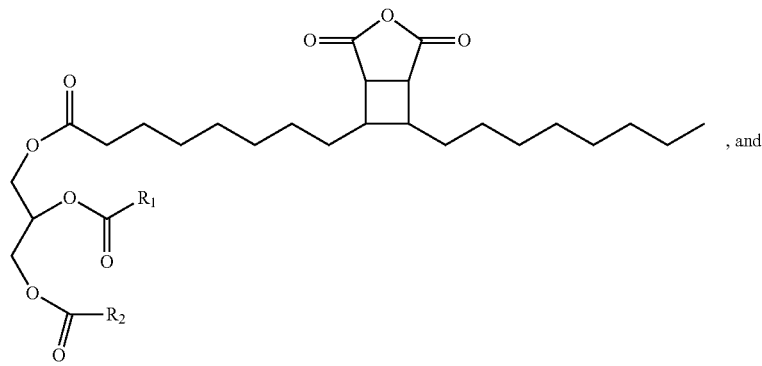

, and wherein the hybrid polyol has a structure (ii)

-continued

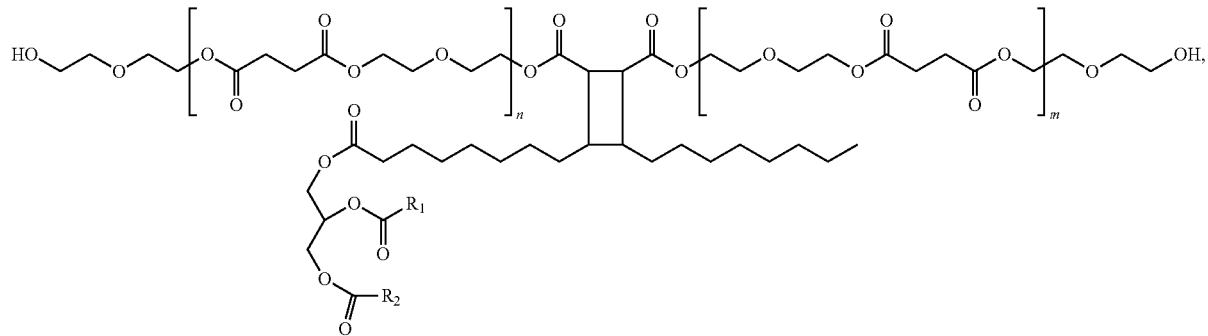

wherein $R_1$ and $R_2$ are independently alkyl chains comprising 9 to 21 carbons, and n and m are independently one or more.

4. The hybrid polyol of claim 1, wherein the polyfunctional carboxylic acid is succinic acid,
wherein the polyhydric alcohol is 1,3-propanediol,
wherein the functionalized natural oil has a structure (i)

wherein $R_1$ and $R_2$ are independently alkyl chains comprising 9 to 21 carbons, and n and m are independently one or more.

5. The hybrid polyol of claim 1, wherein the polyfunctional carboxylic acid is biobased succinic acid, and
wherein the polyhydric alcohol is biobased 1,3-propanediol.

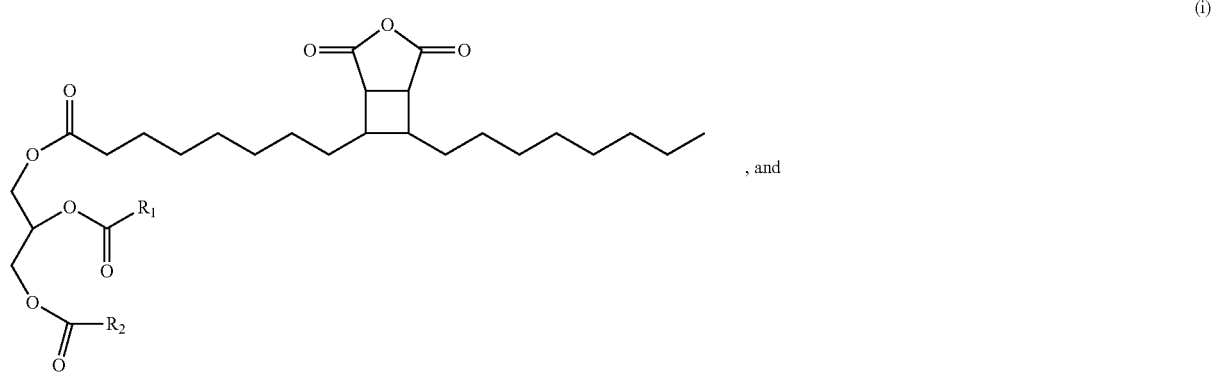

, and wherein the hybrid polyol has a structure (ii)

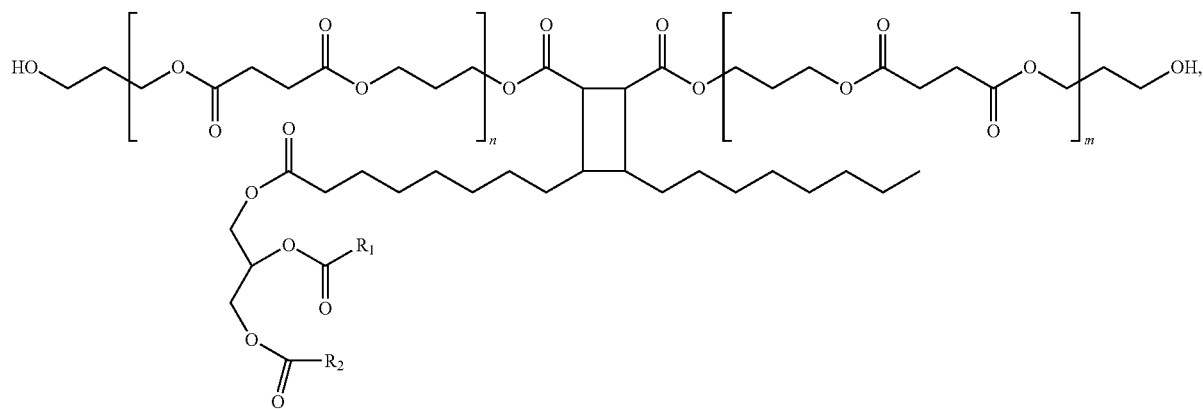

6. The hybrid polyol of claim 1, having at least 10 percent biorenewable content.

7. A polyol mixture, comprising:
the hybrid polyol of claim 1; and
a petroleum-based polyol,
wherein the hybrid polyol is at least 10 percent of the polyol mixture.

8. The polyol mixture of claim 7, wherein the petroleum-based polyol is a polyester polyol.

9. The polyol mixture of claim 7, wherein the petroleum-based polyol is a polyether polyol.

10. A polyol mixture, comprising:
the hybrid polyol of claim 1; and
an isosorbide based polyol,
wherein the isosorbide-based polyol is at least 10% of the polyol mixture.

11. The polyol mixture of claim 10, wherein the isosorbide-based polyol is prepared using bio-based isosorbide.

12. A process for manufacturing the hybrid polyol of claim 1, which is suitable for flexible polyurethane foam manufacturing, the process comprising:
reacting components comprising (a) a functionalized natural oil or natural oil polyol, (b) a polyfunctional carboxylic acid with at least two carboxylic acid groups, and (c) a polyhydric alcohol with at least two hydroxyl groups in the presence of an esterification catalyst to yield the hybrid polyol.

13. The process of claim 12, wherein the functionalized natural oil or natural oil polyol is prepared from a natural oil selected from a group consisting of castor oil, coconut oil, cochin oil, corn oil, cottonseed oil, linseed oil, olive oil, palm oil, palm kernel oil, peanut oil, soybean oil, sunflower oil, tall oils, tallow, *lesquerella* oil, tung oil, whale oil, tea seed oil, sesame seed oil, safflower oil, rapeseed oil, fish oils, any derivatives thereof, and any combinations thereof,
wherein the polyfunctional carboxylic acid is selected from succinic acid, oxalic acid, malonic acid, maleic acid, fumaric acid, glutaric acid, adipic acid, pimelic acid, suberic acid, azelaic acid, citraconic acid, sebacic acid, fumaric acid, malic acid, itaconic acid, muconic acid, citric acid, phthalic acid, isophthalic acid, aconitic acid, propane-1,2,3-tricarboxylic acid, trimesic acid, 2-butynedioic acid, 1,4-cyclohexane dicarboxylic acid, hexahydrophthalic acid, hexachloroendomethylene tetrahydrophthalic acid, dichlorophthalic acid, isophthalic acid, terephthalic acid, trimellitic acid, any derivatives thereof, and any mixtures thereof, and
wherein the polyhydric alcohol is selected from a group consisting of ethylene glycol, propylene glycol, neopentylglycol, butanediol, pentanediol, hexanediol, cyclopentanediol, cyclohexanediol, dimethylol cyclohexane, diethylene glycol, glycerol, trimethylolpropane, butanetriol, pentaerythritol, dipentaerythritol, cyclohexanetriol, 1,3-propanediol, 1,4-butanediol, any mixture thereof, any derivatives thereof, and any combinations thereof.

14. The hybrid polyol of claim 1, wherein the functionalized natural oil or natural oil polyol is derived by subjecting an ethylenically unsaturated natural oil to a free radical mediated grafting reaction involving an ethylenically unsaturated monomer.

15. The hybrid polyol of claim 14 wherein the ethylenically unsaturated monomer is a monomer comprising a carboxyl functional group.

16. The hybrid polyol of claim 14, wherein the ethylenically unsaturated monomer is maleic anhydride.

17. The hybrid polyol of claim 14, wherein the ethylenically unsaturated monomer is a monomer comprising a hydroxyl functional group.

18. The hybrid polyol of claim 1, produced by reacting the functionalized natural oil or natural oil polyol with at least one polyfunctional carboxylic acid and at least one polyhydric alcohol,
wherein the functionalized natural oil or natural oil polyol is derived by subjecting an ethylenically unsaturated natural oil to a free radical mediated grafting reaction involving an ethylenically unsaturated monomer.

\* \* \* \* \*